(12) United States Patent
Lee et al.

(10) Patent No.: US 8,158,803 B2
(45) Date of Patent: Apr. 17, 2012

(54) HETEROCYCLIC ANTIVIRAL COMPOUNDS

(75) Inventors: Eun Kyung Lee, Cupertino, CA (US); Ryan Craig Schoenfeld, San José, CA (US); Francisco Xavier Talamas, Mountain View, CA (US)

(73) Assignee: Roche Palo Alto LLC, South San Francisco, CA (US)

( * ) Notice: Subject to any disclaimer, the term of this patent is extended or adjusted under 35 U.S.C. 154(b) by 190 days.

(21) Appl. No.: 12/766,064

(22) Filed: Apr. 23, 2010

(65) Prior Publication Data

US 2010/0272677 A1 Oct. 28, 2010

Related U.S. Application Data

(60) Provisional application No. 61/172,723, filed on Apr. 25, 2009.

(51) Int. Cl.
*C07D 211/72* (2006.01)
*A61K 31/44* (2006.01)

(52) U.S. Cl. ........................................ 546/290; 514/345

(58) Field of Classification Search ........................ None
See application file for complete search history.

(56) References Cited

FOREIGN PATENT DOCUMENTS

| WO | WO00/09543 | A2 | 2/2000 |
|---|---|---|---|
| WO | WO01/85172 | A1 | 11/2001 |
| WO | 2009032116 | A1 | 3/2009 |
| WO | 2009032123 | A2 | 3/2009 |
| WO | 2009032125 | A1 | 3/2009 |
| WO | 2009039127 | A1 | 3/2009 |
| WO | 2009039134 | A1 | 3/2009 |
| WO | 2009039135 | A1 | 3/2009 |
| WO | WO 2009039135 | A1 * | 3/2009 |
| WO | 2009064848 | A1 | 5/2009 |
| WO | 2009064852 | A1 | 5/2009 |
| WO | 2010010017 | A1 | 1/2010 |
| WO | 2010034671 | A1 | 4/2010 |
| WO | WO2010/111436 | A2 | 9/2010 |
| WO | WO2010/111437 | A1 | 9/2010 |

\* cited by examiner

*Primary Examiner* — Janet Andres
*Assistant Examiner* — Heidi Reese
(74) *Attorney, Agent, or Firm* — Brian L. Buckwalter

(57) ABSTRACT

Compounds having the formula I wherein $R^1$, $R^2$, $R^3$, $R^4$, $R^{5a}$, $R^{5b}$, $R^{5c}$ and $R^6$ are as defined herein are Hepatitis C virus NS5b polymerase inhibitors. Also disclosed are compositions and methods for treating an HCV infection and inhibiting HCV replication.

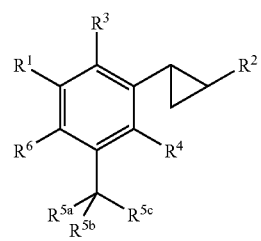

(I)

1 Claim, No Drawings

HETEROCYCLIC ANTIVIRAL COMPOUNDS

CROSS-REFERENCE TO PRIOR APPLICATIONS

This application claims the benefit of priority to U.S. Ser. No. 61/172,723 filed Apr. 25, 2009 which is hereby incorporated by reference in its entirety.

FIELD OF THE INVENTION

The present invention provides non-nucleoside compounds and certain derivatives thereof which are inhibitors of RNA-dependent RNA viral polymerase. These compounds are useful for the treatment of RNA-dependent RNA viral infection. They are particularly useful as inhibitors of hepatitis C virus (HCV) NS5B polymerase, as inhibitors of HCV replication, and for the treatment of hepatitis C infection.

BACKGROUND

Hepatitis C virus is the leading cause of chronic liver disease throughout the world. (Boyer, N. et al., *J. Hepatol.* 2000 32:98-112). The World Health Organization (WHO) estimates that more than 170 million people worldwide (or about 3% of the world's population) are infected with the single-stranded ribonucleic acid (RNA) HCV. (G. M. Lauer, B. D. Walker, *N. Engl. J. Med.* 2001 345:41-52) Approximately one-fifth of chronically infected patients with HCV will eventually develop cirrhosis of the liver, suffering considerable morbidity and mortality, including liver failure and hepatocellular carcinoma (T. J. Liang et al. *Ann. Intern. Med.* 2000 132:296-305; *N. Engl. J. Med.* 347:975-982). HCV infection is the primary indication for liver transplantation in the United States (NIH Consensus Statement on Management of Hepatitis C. 2002; http://www.ncbi.nlm.nih.gov/pubmed/14768714).

HCV has been classified as a member of the virus family Flaviviridae that includes the genera flaviviruses, pestiviruses, and hapaceiviruses which includes hepatitis C viruses (Rice, C. M., Flaviviridae: The viruses and their replication. In: Fields Virology, Editors: B. N. Fields, D. M. Knipe and P. M. Howley, Lippincott-Raven Publishers, Philadelphia, Pa., Chapter 30, 931-959, 1996). HCV is an enveloped virus containing a positive-sense single-stranded RNA genome of approximately 9.4 kb. The viral genome consists of a highly conserved 5' untranslated region (UTR), a long open reading frame encoding a polyprotein precursor of approximately 3011 amino acids, and a short 3' UTR.

Genetic analysis of HCV has identified six main genotypes which diverge by over 30% of the DNA sequence. More than 30 subtypes have been distinguished. In the US approximately 70% of infected individuals have Type 1a and 1b infection. Type 1b is the most prevalent subtype in Asia. (X. Forns and J. Bukh, *Clinics in Liver Disease* 1999 3:693-716; J. Bukh et al., *Semin. Liv. Dis.* 1995 15:41-63). Unfortunately Type 1 infections are more resistant to therapy than either type 2 or 3 genotypes (N. N. Zein, *Clin. Microbiol. Rev.,* 2000 13:223-235).

The HCV genome encodes a polyprotein of 3010-3033, amino acids [Q. L. Choo, et al., *Proc. Natl. Acad. Sci. USA,* 1991 88:2451-2455; N. Kato et al., *Proc. Natl. Acad. Sci. USA* 1990 87:9524-9528; A. Takamizawa et al., *J. Virol.* 1991 65:1105-1113). Viral structural proteins include a nucleocapsid core protein (C) and two envelope glycoproteins, E1 and E2. HCV also encodes two proteases, a zinc-dependent metalloproteinase encoded by the NS2-NS3 region and a serine protease encoded in the NS3 region. The HCV NS3 protease is a serine protease that helps process the majority of the viral enzymes, and is thus considered essential for viral replication and infectivity. These proteases are required for cleavage of specific regions of the precursor polyprotein into mature peptides. The carboxyl half of nonstructural protein 5, NS5B, contains the RNA-dependent RNA polymerase.

Currently a limited number of approved therapies are available for the treatment of HCV infection. New and existing therapeutic approaches for treating HCV infection and inhibiting of HCV NS5B polymerase activity have been reviewed: R. G. Gish, *Sem. Liver. Dis.,* 1999 19:5; Di Besceglie, A. M. and Bacon, B. R., *Scientific American,* October: 1999 80-85; G. Lake-Bakaar, *Curr. Drug Targ. Infect Dis.* 2003 3(3):247-253; P. Hoffmann et al, *Exp. Opin. Ther. Patents* 2003 13(11): 1707-1723; M. P. Walker et al., *Exp. Opin. Investing. Drugs* 2003 12(8):1269-1280; S.-L. Tan et al., *Nature Rev. Drug Discov.* 2002 1:867-881; J. Z. Wu and Z. Hong, *Curr. Drug Targ-Infect. Dis.* 2003 3(3):207-219.

Ribavirin (1-((2R,3R,4S,5R)-3,4-Dihydroxy-5-hydroxymethyl-tetrahydro-furan-2-yl)-1H-[1,2,4]triazole-3-carboxylic acid amide; Virazole®) is a synthetic, non-interferon-inducing, broad-spectrum antiviral nucleoside analog. Ribavirin has in vitro activity against several DNA and RNA viruses including Flaviviridae (Gary L. Davis. *Gastroenterology* 2000 118:S104-S114). Although, in monotherapy ribavirin reduces serum amino transferase levels to normal in 40% of patients, it does not lower serum levels of HCV-RNA. Ribavirin also exhibits significant toxicity and is known to induce anemia. Viramidine is a ribavirin prodrug converted ribavirin by adenosine deaminase to in hepatocytes. (J. Z. Wu, *Antivir. Chem. Chemother.* 2006 17(1):33-9)

Interferons (IFNs) have been available for the treatment of chronic hepatitis for nearly a decade. IFNs are glycoproteins produced by immune cells in response to viral infection. Two distinct types of interferon are recognized: Type 1 includes several interferon alphas and one interferon beta, type 2 includes interferon gamma. Type 1 interferons are produced mainly by infected cells and protect neighboring cells from de novo infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary. Cessation of therapy results in a 70% relapse rate and only 10-15% exhibit a sustained virological response with normal serum alanine transferase levels. (Davis, Luke-Bakaar, supra)

Combination therapy of HCV with ribavirin and interferon-α currently is the standard of care for treatment-naïve patients HCV. Combining ribavirin and PEG-IFN (infra) results in a sustained viral response (SVR) defined as undetectable hepatitis C virus ribonucleic acid (HCV RNA) 24 weeks after completion of therapy (Fried M W, et al. *N. Engl. J. Med.* 2002 347:975-982) in 54-56% of patients with type 1 HCV. The SVR approaches 80% for type 2 and 3 HCV. (Walker, supra) Furthermore, PEG-IFN is given by injection, and the hematologic and constitutional toxicities of PEG-IFN and of RBV are difficult for many patients to tolerate for the long (up to 48 weeks) duration of treatment required. Currently, there is no SOC treatment for patients who either relapsed or did not respond to (nonresponders) PEG-IFN/RBV therapy. Given the high prevalence of CHC disease worldwide, the high treatment failure rate with the current SOC, and tolerability issues with the current SOC, there is a substantial unmet medical need to improve and expand therapeutic options for these patient populations. The effectiveness of the host defenses is hampered by the ability of HCV to disrupt, evade, and antagonize the host immune response, not only ensuring continued viral infection, but also quite often resisting the antiviral action of IFN therapy (M. Gale, Jr., E. M. Foy, *Nature* 2005. 436:939-945). Therefore, a strategy that targets the virus itself may improve the results of therapy in comparison with current therapy options.

A number of potential new molecular targets for drug development as anti-HCV therapeutics have now been identified including, but not limited to, the NS2-NS3 autoprotease, the NS3 protease, the NS3 helicase, NS5A and the NS5B polymerase. The RNA-dependent RNA polymerase is absolutely essential for replication of the single-stranded, positive sense, RNA genome. This enzyme has elicited significant interest among medicinal chemists.

SUMMARY OF THE INVENTION

There is currently no preventive treatment of Hepatitis C virus (HCV) and currently approved therapies, which exist only against HCV, are limited. Design and development of new pharmaceutical compounds is essential.

The present invention provides a compound according to formula I, or a pharmaceutically acceptable salt thereof, wherein:

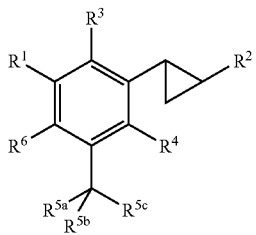

(I)

$R^1$ is a heteroaryl radical selected from the group consisting of 2-oxo-1,2-dihydro-pyridin-3-yl, 3-oxo-3,4-dihydro-pyrazin-2-yl, 3-oxo-2,3-dihydro-pyridazin-4-yl, 2-oxo-1,2-dihydro-pyrimidin-4-one-5-yl and 2,4-dioxo-1,2,3,4-tetrahydro-pyrimidin-5-yl said heteroaryl being optionally substituted by halogen, $C_{1-6}$ alkyl, $C_{1-3}$ haloalkyl or $C_{1-6}$ alkoxy.

$R^2$ is (hetero)aryl radical selected from the group consisting of phenyl, pyridinyl, pyrimidinyl, pyrazinyl and pyridazinyl said (hetero)aryl radical optionally independently substituted with one to three substituents selected from the group consisting of hydroxy, $C_{1-6}$ alkoxy, $C_{1-6}$ alkyl, $C_{1-6}$ hydroxyalkyl, $C_{1-3}$ alkoxy-$C_{1-6}$ alkyl, halogen, $(CH_2)_n NR^a R^b$, cyano, $C_{1-6}$ alkoxycarbonyl, carbamoyl, N-alkylcarbamoyl, N,N-dialkylcarbamoyl, carboxyl, carboxyl-$C_{1-3}$ alkyl, $SO_2NH_2$, $C_{1-6}$ alkylsulfinyl and $C_{1-6}$ alkylsulfonyl and n is zero to three;

$R^3$ is hydrogen, hydroxy, $C_{1-3}$ hydroxyalkyl or cyano.

$R^4$ is hydrogen, $C_{1-6}$ alkyl, $C_{1-6}$ haloalkyl, $C_{1-6}$ alkoxy, $C_{1-6}$ haloalkoxy, halogen or $R^4$ and $R^{5a}$ together are $CH_2$—O and together with atoms to which they are attached form a 2,3-dihydrobenzofuran.

$R^{5a}$, $R^{5b}$ and $R^{5c}$ (i) when taken independently are selected independently from $C_{1-3}$ alkyl, $C_{1-2}$ alkoxy, $C_{1-2}$ fluoroalkyl, hydroxy or halogen or (ii) when taken together, $R^{5a}$ and $R^{5b}$ together are $C_{2-4}$ methylene and $R^{5c}$ is $C_{1-3}$ alkyl, $C_{1-2}$ alkoxy, $C_{1-2}$ fluoroalkyl or halogen, or (iii). either $R^6$ or $R^4$ and $R^{5a}$ together are $CH_2$—O and together with atoms to which they are attached for a 2,3-dihydro-benzofuran and $R^{5b}$ and $R^{5c}$ are $C_{1-3}$ alkyl.

$R^6$ is hydrogen, fluorine or $R^6$ and $R^{5a}$ together are $CH_2$—O and together with atoms to which they are attached form a 2,3-dihydrobenzofuran.

$R^a$ and $R^b$ are independently in hydrogen, $C_{1-6}$ alkyl, $C_{1-6}$ haloalkyl, $C_{1-6}$ acyl, $C_{1-6}$ alkylsulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl, $C_{1-6}$ alkoxy-$C_{1-6}$ alkylsulfonyl, sulfamoyl, $C_{1-3}$ alkylsulfamoyl, $C_{1-3}$ dialkylsulfamoyl, carbamoyl, $C_{1-3}$ alkylcarbamoyl or $C_{1-3}$ dialkylcarbamoyl.

The present invention further comprises pharmaceutically acceptable salts of the compounds described herein.

The present invention also provides a method for treating a disease caused by the Hepatitis C Virus (HCV) virus by administering a therapeutically effective quantity of a compound according to formula I to a patient in need thereof. The compound can be administered alone or co-administered with other antiviral compounds or immunomodulators.

The present invention also provides a method for inhibiting replication of HCV in a cell by administering a compound according to formula I in an amount effective to inhibit HCV.

The present invention also provides a pharmaceutical composition comprising a compound according to formula I and at least one pharmaceutically acceptable carrier, diluent or excipient.

DETAILED DESCRIPTION OF THE INVENTION

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The phrase "as defined herein above" refers to the broadest definition for each group as provided in the Summary of the Invention or the broadest claim. In all other embodiments provided below, substituents which can be present in each embodiment and which are not explicitly defined retain the broadest definition provided in the Summary of the Invention.

In this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

The term "independently" is used herein to indicate that a variable is applied in any one instance without regard to the presence or absence of a variable having that same or a different definition within the same compound. Thus, in a compound in which R" appears twice and is defined as "independently carbon or nitrogen", both R"s can be carbon, both R"s can be nitrogen, or one R" can be carbon and the other nitrogen.

When any variable (e.g., $R^1$, $R^{4a}$, Ar, $X^1$ or Het) occurs more than one time in any moiety or formula depicting and describing compounds employed or claimed in the present invention, its definition on each occurrence is independent of its definition at every other occurrence. Also, combinations of substituents and/or variables are permissible only if such compounds result in stable compounds.

The symbols "*" at the end of a bond or " - - - " drawn through a bond each refer to the point of attachment of a functional group or other chemical moiety to the rest of the molecule of which it is a part. Thus, for example:

MeC(═O)OR⁴ wherein R⁴ =

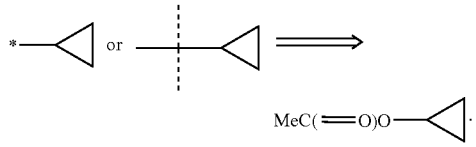

A bond drawn into ring system (as opposed to connected at a distinct vertex) indicates that the bond may be attached to any of the suitable ring atoms.

The term "optional" or "optionally" as used herein means that a subsequently described event or circumstance may, but need not, occur, and that the description includes instances where the event or circumstance occurs and instances in which it does not. For example, "optionally substituted" means that the optionally substituted moiety may incorporate a hydrogen or a substituent.

The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

As used herein, the recitation of a numerical range for a variable is intended to convey that the invention may be practiced with the variable equal to any of the values within that range. Thus, for a variable which is inherently discrete, the variable can be equal to any integer value of the numerical range, including the end-points of the range. Similarly, for a variable which is inherently continuous, the variable can be equal to any real value of the numerical range, including the end-points of the range. As an example, a variable which is described as having values between 0 and 2, can be 0, 1 or 2 for variables which are inherently discrete, and can be 0.0, 0.1, 0.01, 0.001, or any other real value for variables which are inherently continuous.

Compounds of formula I exhibit tautomerism. Tautomeric compounds can exist as two or more interconvertable species. Prototropic tautomers result from the migration of a covalently bonded hydrogen atom between two atoms. Tautomers generally exist in equilibrium and attempts to isolate an individual tautomers usually produce a mixture whose chemical and physical properties are consistent with a mixture of compounds. The position of the equilibrium is dependent on chemical features within the molecule. For example, in many aliphatic aldehydes and ketones, such as acetaldehyde, the keto form predominates while; in phenols, the enol form predominates. Common prototropic tautomers include keto/enol (—C(═O)—CH—⇌—C(—OH)═CH—), amide/imidic acid (—C(═O)—NH—⇌—C(—OH)═N—) and amidine (—C(═NR)—NH—⇌—C(—NHR)═N—) tautomers. The latter two are particularly common in heteroaryl and heterocyclic rings and the present invention encompasses all tautomeric forms of the compounds.

It will be appreciated by the skilled artisan that some of the compounds of formula I may contain one or more chiral centers and therefore exist in two or more stereoisomeric forms. The racemates of these isomers, the individual isomers and mixtures enriched in one enantiomer, as well as diastereomers when there are two chiral centers, and mixtures partially enriched with specific diastereomers are within the scope of the present invention. The present invention includes all the individual stereoisomers (e.g. enantiomers), racemic mixtures or partially resolved mixtures of the compounds of formulae I and, where appropriate, the individual tautomeric forms thereof.

The racemates can be used as such or can be resolved into their individual isomers. The resolution can afford stereochemically pure compounds or mixtures enriched in one or more isomers. Methods for separation of isomers are well known (cf. Allinger N. L. and Eliel E. L. in "*Topics in Stereochemistry*", Vol. 6, Wiley Interscience, 1971) and include physical methods such as chromatography using a chiral adsorbent. Individual isomers can be prepared in chiral form from chiral precursors. Alternatively individual isomers can be separated chemically from a mixture by forming diastereomeric salts with a chiral acid, such as the individual enantiomers of 10-camphorsulfonic acid, camphoric acid, .alpha.-bromocamphoric acid, tartaric acid, diacetyltartaric acid, malic acid, pyrrolidone-5-carboxylic acid, and the like, fractionally crystallizing the salts, and then freeing one or both of the resolved bases, optionally repeating the process, so as obtain either or both substantially free of the other; i.e., in a form having an optical purity of >95%. Alternatively the racemates can be covalently linked to a chiral compound (auxiliary) to produce diastereomers which can be separated by chromatography or by fractional crystallization after which time the chiral auxiliary is chemically removed to afford the pure enantiomers.

The compounds of formula I may contain an acidic or basic functional groups. Suitable acid addition salts are formed by protonation of a basic center with an acid. Deprotonation of an acidic center by a base likewise forms a salt. Salt formation may confer a desirable pharmacokinetic property on the active ingredient which were absent in the non-salt form, and may even positively affect the pharmacodynamics of the active ingredient with respect to its therapeutic activity in the body. The phrase "pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. For a review on suitable salts see Berge et al, *J. Pharm. Sci.*, 1977 66:1-19 and G. S. Paulekuhn et al. *J. Med. Chem.* 2007 50:6665.

Technical and scientific terms used herein have the meaning commonly understood by one of skill in the art to which the present invention pertains, unless otherwise defined. Reference is made herein to various methodologies and materials known to those of skill in the art. Standard reference works setting forth the general principles of pharmacology include Goodman and Gilman's *The Pharmacological Basis of Therapeutics*, 10th Ed., McGraw Hill Companies Inc., New York (2001). The starting materials and reagents used in preparing these compounds generally are either available from commercial suppliers, such as Aldrich Chemical Co., or are prepared by methods known to those skilled in the art following procedures set forth in references. Materials, reagents and the like to which reference are made in the following description and examples are obtainable from commercial sources, unless otherwise noted. General synthetic procedures have been described in treatise such as *Fieser and Fieser's Reagents for Organic Synthesis*; Wiley & Sons: New York, Volumes 1-21; R. C. LaRock, *Comprehensive Organic Transformations*, 2nd edition Wiley-VCH, New York 1999; *Comprehensive Organic Synthesis*, B. Trost and I. Fleming (Eds.) vol. 1-9 Pergamon, Oxford, 1991; *Comprehensive Heterocyclic Chemistry*, A. R. Katritzky and C. W. Rees (Eds) Pergamon, Oxford 1984, vol. 1-9; *Comprehensive Heterocyclic Chemistry II*, A. R. Katritzky and C. W. Rees (Eds) Pergamon, Oxford 1996, vol. 1-11; and *Organic Reactions*, Wiley & Sons: New York, 1991, Volumes 1-40 and will be familiar to those skilled in the art.

In one embodiment of the present invention there is provided a compound according to formula I wherein $R^1$, $R^2$, $R^3$, $R^4$, $R^{5a}$, $R^{5b}$, $R^{5c}$, $R^6$, $R^a$, $R^b$ and n are as described herein above.

In another embodiment of the present invention there is provided a compound according to formula I wherein $R^1$ is 2-oxo-1,2-dihydro-pyridin-3-yl, 3-oxo-3,4-dihydro-pyrazin-2-yl, 3-oxo-2,3-dihydro-pyridazin-4-yl, and 2,4-dioxo-1,2,3,4-tetrahydro-pyrimidin-5-yl; $R^2$ is optionally substituted phenyl or optionally substituted pyridinyl; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound according to formula I wherein $R^1$ is 2-oxo-1,2-dihydro-pyridin-3-yl, 3-oxo-3,4-dihydro-pyrazin-2-yl, 3-oxo-2,3-dihydro-pyridazin-4-yl, and 2,4-dioxo-1,2,3,4-tetrahydro-pyrimidin-5-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In an embodiment of the present invention there is provided a compound according to formula I wherein $R^1$ is 2-oxo-1,2-dihydro-pyridin-3-yl or 3-oxo-2,3-dihydro-pyridazin 4-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^4$ is hydrogen or $C_{1-6}$ alkoxy; $R^3$ is hydrogen or hydroxy; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound according to formula I wherein $R^1$ is 2-oxo-1,2-dihydro-pyridin-3-yl or 3-oxo-2,3-dihydro-pyridazin 4-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^4$ is hydrogen or $C_{1-6}$ alkoxy; $R^3$ is hydrogen or hydroxy; and $R^{5a}$, $R^{5b}$ and $R^{5c}$ are methyl.

In another embodiment of the present invention there is provided a compound according to formula I wherein $R^1$ is 2-oxo-1,2-dihydro-pyridin-3-yl or 3-oxo-2,3-dihydro-pyridazin 4-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^4$ is hydrogen or $C_{1-6}$ alkoxy; $R^3$ is hydrogen or hydroxy; and $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound according to formula I wherein $R^1$ is 2-oxo-1,2-dihydro-pyridin-3-yl or 3-oxo-2,3-dihydro-pyridazin 4-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^4$ is hydrogen or $C_{1-6}$ alkoxy; $R^3$ is hydrogen or hydroxy; and, $R^{5a}$ and $R^{5b}$ together are $(CH_2)_2$ and $R^{5c}$ is methyl, difluoromethyl, trifluoromethyl or chloro.

In another embodiment of the present invention there is provided a compound according to formula I wherein $R^1$ is 2-oxo-1,2-dihydro-pyridin-3-yl or 3-oxo-2,3-dihydro-pyridazin 4-yl; $R^2$ is pyrimidinyl, pyrazinyl and pyridazinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^3$ is hydrogen or hydroxy; $R^4$ is hydrogen or $C_{1-6}$ alkoxy; and, $R^{5a}$, $R^{5b}$ and $R^{5c}$ are methyl.

In another embodiment of the present invention there is provided a compound according to formula I wherein $R^1$ is optionally substituted 3-oxo-3,4-dihydro-pyrazin-2-yl, or 2,4-dioxo-1,2,3,4-tetrahydro-pyrimidin-5-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^3$ is hydrogen or hydroxy; $R^4$ is hydrogen or $C_{1-6}$ alkoxy; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound according to formula I wherein $R^1$ is optionally substituted 3-oxo-3,4-dihydro-pyrazin-2-yl, or 2,4-dioxo-1,2,3,4-tetrahydro-pyrimidin-5-yl; $R^2$ is pyrimidinyl, pyrazinyl and pyridazinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^3$ is hydrogen or hydroxy; $R^4$ is hydrogen or $C_{1-6}$ alkoxy; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound according to formula I wherein $R^1$ is optionally substituted 2-oxo-1,2-dihydro-pyrimidin-4-one-5-yl; $R^2$ is phenyl or pyridinyl substituted at least by $(CH_2)_nNR^aR^b$ wherein n is 0 or 1 and $R^a$ is hydrogen and $R^b$ is $C_{1-6}$ sulfonyl, $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl; $R^3$ is hydrogen or hydroxy; $R^4$ is hydrogen or $C_{1-6}$ alkoxy; and $R^{5a}$, $R^{5b}$ and $R^{5c}$ are (i) independently $C_{1-3}$ alkyl or $C_{1-3}$ haloalkyl or (ii) $R^{5a}$ and $R^{5b}$ together are $(CH_2)_2$ and $R^{5c}$ is $C_{1-3}$ alkyl, $C_{1-3}$ haloalkyl or halogen.

In another embodiment of the present invention there is provided a compound selected from I-1 to I-5 in TABLE I In another embodiment of the present invention there is provided a method of treating a HCV infection in a patient in need thereof comprising administering a therapeutically effective amount of a compound according to formula I wherein $R^1$, $R^2$, $R^3$, $R^4$, $R^{5a}$, $R^{5b}$, $R^{5c}$, $R^6$, $R^a$, $R^b$ and n are as defined hereinabove.

In another embodiment of the present invention there is provided a method of treating a HCV infection in a patient in need thereof comprising co-administering a therapeutically effective amount of a compound according to formula I wherein $R^1$, $R^2$, $R^3$, $R^4$, $R^{5a}$, $R^{5b}$, $R^{5c}$, $R^6$, $R^a$, $R^b$ and n are as defined herein above and at least one immune system modulator and/or at least one antiviral agent that inhibits replication of HCV.

In another embodiment of the present invention there is provided a method of treating a disease caused by HCV in a patient in need thereof comprising co-administering a therapeutically effective amount of a compound according to formula I wherein $R^1$, $R^2$, $R^3$, $R^4$, $R^{5a}$, $R^{5b}$, $R^{5c}$, $R^6$, $R^a$, $R^b$ and n are as defined herein above and at least one immune system modulator selected from interferon, interleukin, tumor necrosis factor or colony stimulating factor.

In another embodiment of the present invention there is provided a method of treating a HCV infection in a patient in need thereof comprising co-administering a therapeutically effective amount of a compound according to formula I wherein $R^1$, $R^2$, $R^3$, $R^4$, $R^{5a}$, $R^{5b}$, $R^{5c}$, $R^6$, $R^a$, $R^b$ and n are as defined herein above and an interferon or chemically derivatized interferon.

In another embodiment of the present invention there is provided a method of treating a HCV infection in a patient in need thereof comprising co-administering a therapeutically effective amount of a compound according to formula I wherein $R^1$, $R^2$, $R^3$, $R^4$, $R^{5a}$, $R^{5b}$, $R^{5c}$, $R^6$, $R^a$, $R^b$ and n are as defined herein above and another antiviral compound selected from the group consisting of a HCV protease inhibitor, another HCV polymerase inhibitor, a HCV helicase inhibitor, a HCV primase inhibitor and a HCV fusion inhibitor.

In another embodiment of the present invention there is provided a method for inhibiting viral replication in a cell by delivering a therapeutically effective amount of a compound of the formula I wherein $R^1$, $R^2$, $R^3$, $R^4$, $R^{5a}$, $R^{5b}$, $R^{5c}$, $R^6$, $R^a$, $R^b$ and n are as defined herein above admixed with at least one pharmaceutically acceptable carrier, diluent or excipient.

In another embodiment of the present invention there is provided a composition comprising a compound according to formula I wherein $R^1$, $R^2$, $R^3$, $R^4$, $R^{5a}$, $R^{5b}$, $R^{5c}$, $R^6$, $R^a$, $R^b$ and n are as defined herein above admixed with at least one pharmaceutically acceptable carrier, diluent or excipient.

The term "alkyl" as used herein without further limitation alone or in combination with other groups, denotes an unbranched or branched chain, saturated, monovalent hydrocarbon residue containing 1 to 10 carbon atoms. The term "lower alkyl" denotes a straight or branched chain hydrocarbon residue containing 1 to 6 carbon atoms. "$C_{1-6}$ alkyl" as used herein refers to an alkyl composed of 1 to 6 carbons. Examples of alkyl groups include, but are not limited to, lower alkyl groups include methyl, ethyl, propyl, iso-propyl, n-butyl, iert-butyl, tert-butyl, neopentyl, hexyl, and octyl.

The definitions described herein may be appended to form chemically-relevant combinations, such as "heteroalkylaryl," "haloalkylheteroaryl," "arylalkylheterocyclyl," "alkylcarbonyl," "alkoxyalkyl," and the like. When the term "alkyl" is used as a suffix following another term, as in "phenylalkyl," or "hydroxyalkyl," this is intended to refer to an alkyl group, as defined above, being substituted with one to two substituents selected from the other specifically-named group. Thus, for example, "phenylalkyl" refers to an alkyl group having one to two phenyl substituents, and thus includes benzyl, phenylethyl, and biphenyl. An "alkylaminoalkyl" is an alkyl group having one to two alkylamino substituents. "Hydroxyalkyl" includes 2-hydroxyethyl, 2-hydroxypropyl, 1-(hydroxymethyl)-2-methylpropyl, 2-hydroxybutyl, 2,3-dihydroxybutyl, 2-(hydroxymethyl), 3-hydroxypropyl, and so forth. Accordingly, as used herein, the term "hydroxyalkyl" is used to define a subset of heteroalkyl groups defined below. The term -(ar)alkyl refers to either an unsubstituted alkyl or an aralkyl group. The term (hetero)aryl or (hetero)aryl refers to either an aryl or a heteroaryl group.

The term "alkylene" as used herein denotes a divalent saturated linear hydrocarbon radical of 1 to 10 carbon atoms (e.g., $(CH_2)_n$) or a branched saturated divalent hydrocarbon radical of 2 to 10 carbon atoms (e.g., —CHMe- or —CH$_2$CH (i-Pr)CH$_2$—), unless otherwise indicated. $C_{0-4}$ alkylene refers to a linear or branched saturated divalent hydrocarbon radical comprising 1-4 carbon atoms or, in the case of $C_0$, the alkylene radical is omitted. Except in the case of methylene, the open valences of an alkylene group are not attached to the same atom. Examples of alkylene radicals include, but are not limited to, methylene, ethylene, propylene, 2-methyl-propylene, 1,1-dimethyl-ethylene, butylene, 2-ethylbutylene.

The term "alkoxy" as used herein means an —O-alkyl group, wherein alkyl is as defined above such as methoxy, ethoxy, n-propyloxy, i-propyloxy, n-butyloxy, i-butyloxy, t-butyloxy, pentyloxy, hexyloxy, including their isomers. "Lower alkoxy" as used herein denotes an alkoxy group with a "lower alkyl" group as previously defined. "$C_{1-10}$ alkoxy" as used herein refers to an —O-alkyl wherein alkyl is $C_{1-10}$.

The term "haloalkyl" as used herein denotes an unbranched or branched chain alkyl group as defined above wherein 1, 2, 3 or more hydrogen atoms are substituted by a halogen. Examples are 1-fluoromethyl, 1-chloromethyl, 1-bromomethyl, 1-iodomethyl, difluoromethyl, trifluoromethyl, trichloromethyl, 1-fluoroethyl, 1-chloroethyl, 1 2-fluoroethyl, 2-chloroethyl, 2-bromoethyl, 2,2-dichloroethyl, 3-bromopropyl or 2,2,2-trifluoroethyl. The term "fluoroalkyl" as used herein refers to a haloalkyl moiety wherein fluorine is the halogen.

The term "haloalkoxy" as used herein refers to a group —OR where R is haloalkyl as defined herein. The term "haloalkylthio" as used herein refers to a group —SR where R is haloalkyl as defined herein.

The term "halogen" or "halo" as used herein means fluorine, chlorine, bromine, or iodine.

The terms "hydroxyalkyl" and "alkoxyalkyl" as used herein denotes alkyl radical as herein defined wherein one to three hydrogen atoms on different carbon atoms is/are replaced by hydroxyl or alkoxy groups respectively. A $C_{1-3}$ alkoxy-$C_{1-6}$ alkyl moiety refers to a $C_{1-6}$ alkyl substituent in which 1 to 3 hydrogen atoms are replaced by a $C_{1-3}$ alkoxy and the point of attachment of the alkoxy is the oxygen atom.

The terms "alkoxycarbonyl" and "aryloxycarbonyl" as used herein denotes a group of formula —C(=O)OR wherein R is alkyl or aryl respectively and alkyl and aryl are as defined herein.

The term "cyano" as used herein refers to a carbon linked to a nitrogen by a triple bond, i.e., —C≡N. The term "nitro" as used herein refers to a group —NO$_2$. The term "carboxy" as used herein refers to a group —CO$_2$H.

The term oxo refers to a doubly bonded oxygen (=O), i.e. a carbonyl group.

The term "acyl" (or "alkanoyl") as used herein denotes a group of formula —C(=O)R wherein R is hydrogen or lower alkyl as defined herein. The term or "alkylcarbonyl" as used herein denotes a group of formula C(=O)R wherein R is alkyl as defined herein. The term $C_{1-6}$ acyl or "alkanoyl" refers to a group —C(=O)R contain 1 to 6 carbon atoms. The $C_1$ acyl group is the formyl group wherein R=H and a C6 acyl group refers to hexanoyl when the alkyl chain is unbranched. The term "arylcarbonyl" or "aroyl" as used herein means a group of formula C(=O)R wherein R is an aryl group; the term "benzoyl" as used herein an "arylcarbonyl" or "aroyl" group wherein R is phenyl.

The terms "alkylsulfonyl" and "arylsulfonyl" as used herein denotes a group of formula —S(=O)$_2$R wherein R is alkyl or aryl respectively and alkyl and aryl are as defined herein. The term $C_{1-3}$ alkylsulfonylamido as used herein refers to a group RSO$_2$NH— wherein R is a $C_{1-3}$ alkyl group as defined herein. The terms $C_{1-6}$ haloalkylsulfonyl, $C_{3-7}$ cycloalkylsulfonyl, $C_{3-7}$ cycloalkyl-$C_{1-3}$ alkyl-sulfonyl or $C_{1-6}$ alkoxy-$C_{1-6}$ alkylsulfonyl refer to a compound, S(=O)$_2$R wherein R is $C_{1-6}$ haloalkyl, $C_{3-7}$ cycloalkyl, $C_{3-7}$ cycloalkyl-$C_{1-3}$ alkyl and $C_{1-6}$ alkoxy-$C_{1-6}$ alkyl, respectively.

The terms "alkylsulfonylamino" and "arylsulfonylamino" as used herein denotes a group of formula —NR'S(=O)$_2$R wherein R is alkyl or aryl respectively, R' is hydrogen or $C_{1-3}$ alkyl, and alkyl and aryl are as defined herein.

The term "sulfamoyl" as used herein refers to the radical —S(O)$_2$NH$_2$. The terms "N-alkylsulfamoyl" and "N,N-dialkylsulfamoyl" as used herein refers to the radical —S(O)$_2$NR'R", wherein R' and R" are hydrogen and lower alkyl and R' and R" are independently lower alkyl respectively. Examples of N-alkylsulfamoyl substituents include, but are not limited to methylaminosulfonyl, iso-propylaminosulfonyl. Examples of N,N-dialkylsulfamoyl substituents include, but are not limited to dimethylaminosulfonyl, iso-propylmethylaminosulfonyl.

The term "carbamoyl" as used herein means the radical —CONH$_2$. The prefix "N-alkylcabamoyl" and "N,N-dialkylcarbamoyl" means a radical CONHR' or CONR'R" respectively wherein the R' and R" groups are independently alkyl as defined herein. The prefix N-arylcabamoyl" denotes the radical CONHR' wherein R' is an aryl radical as defined herein.

The term "(hetero)aryl" as used herein refers to a ring which is either an aromatic ring or a heteroaromatic ring. The term "1,2-diarylcyclopropanes" as used herein refers to all compounds encompassed in claim 1 without limitation.

The term "pyridine" ("pyridinyl") refers to a six-membered heteroaromatic ring with one nitrogen atom. The terms "pyrimidine" (pyrimidinyl), "pyrazine" ("pyrazinyl") and "pyridazine" ("pyridazinyl") refer to a six-membered non-fused heteroaromatic ring with two nitrogen atoms disposed in a 1,3, a 1,4 and a 1,2 relationship respectively. The respective radical names are in parentheses.

The terms (i) 3-oxo-3,4-dihydro-pyrazin-2-yl, (ii) 3-oxo-2,3-dihydro-pyridazin-4-yl, (iii) 6-oxo-1,6-dihydro-pyrimidin-5-yl, (iv) 6-oxo-1,6-dihydro-[1,2,4]triazin-5-yl, (v) 2,4-dioxo-1,2,3,4-tetrahydro-pyrimidin-5-yl and (vi) 2-oxo-1,2-dihydro-pyridin-3-yl, as used herein refer to the following moieties:

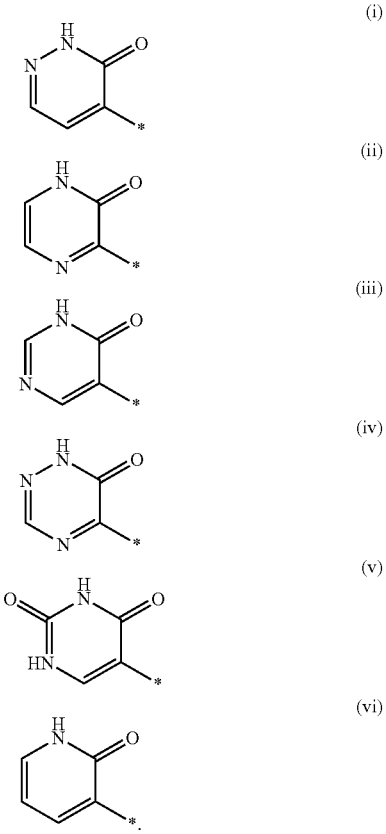

The phrase "substituted at least by (CH$_2$)$_n$NR$_c$R$^d$" in reference to Ar$^1$ simply indicates the ring is substituted by (CH$_2$)$_n$ NR$_c$R$^d$ but other additional optional substitutions within the scope of the claim are permitted.

In one embodiment, the compounds of the present invention according to formula I are used in combination with other active therapeutic ingredients or agents to treat patients with an HCV viral infection. According to the present invention, the active therapeutic ingredient used in combination with the compound of the present invention can be any agent having a therapeutic effect when used in combination with the compound of the present invention. For example, the active agent used in combination with the compound of the present invention can be interferons, ribavirin analogs, HCV NS3 protease inhibitors, nucleoside inhibitors of HCV polymerase, non-nucleoside inhibitors of HCV polymerase, and other drugs for treating HCV, or mixtures thereof.

Examples of the nucleoside NS5b polymerase inhibitors include, but are not limited to NM-283, valopicitabine, R1626, PSI-6130 (R1656), R-7128, IDX184 and IDX102 (Idenix) BILB 1941.

Examples of the non-nucleoside NS5b polymerase inhibitors include, but are not limited to HCV-796 (ViroPharma and Wyeth), MK-0608, MK-3281 (Merck), NM-107, R7128 (R4048), VCH-759 (ViroChem), GSK625433 and GSK625433 (Glaxo), PF-868554 (Pfizer), GS-9190 (Gilead), A-837093 and A848837 (Abbot Laboratories), ANA598 (Anadys Pharmaceuticals); GL100597 (GNLB/NVS), VBY 708 (ViroBay), benzimidazole derivatives (H. Hashimoto et al. WO 01/47833, H. Hashimoto et al. WO 03/000254, P. L. Beaulieu et al. WO 03/020240 A2; P. L. Beaulieu et al. U.S. Pat. No. 6,448,281 B1; P. L. Beaulieu et al. WO 03/007945 A1), benzo-1,2,4-thiadiazine derivatives (D. Dhanak et al.

WO 01/85172 A1, filed May 10, 2001; D. Chai et al., WO2002098424, filed Jun. 7, 2002, D. Dhanak et al. WO 03/037262 A2, filed Oct. 28, 2002; K. J. Duffy et al. WO03/099801 A1, filed May 23, 2003, M. G. Darcy et al. WO2003059356, filed Oct. 28, 2002; D. Chai et al. WO 2004052312, filed Jun. 24, 2004, D. Chai et al. WO2004052313, filed Dec. 13, 2003; D. M. Fitch et al., WO2004058150, filed Dec. 11, 2003; D. K. Hutchinson et al. WO2005019191, filed Aug. 19, 2004; J. K. Pratt et al. WO 2004/041818 A1, filed Oct. 31, 2003), 1,1-dioxo-4H-benzo[1,4]thiazin-3-yl derivatives (J. F. Blake et al. in U.S. Patent Publication US20060252785 and 1,1-dioxo-benzo[d]isothazol-3-yl compounds (J. F. Blake et al. in U.S. Patent Publication 2006040927).

Inhibitors of the HCV NS3 protease also have been identified as potentially useful for treatment of HCV. Protease inhibitors in clinical trials include VX-950 (Telaprevir, Vertex), SCH503034 (Broceprevir, Schering), TMC435350 (Tibotec/Medivir) and ITMN-191 (Intermune). Other protease inhibitors in earlier stages of development include MK7009 (Merck), BMS-605339 and BMS-790052 (Bristol Myers Squibb), VBY-376 (Virobay), IDXSCA/IDXSCB (Idenix), BI12202 and BILN-2065 (Boehringer-Ingelheim), VX-500 (Vertex), PHX1766 Phenomix).

Examples of the interferons include, but are not limited to pegylated rIFN-alpha 2b, pegylated rIFN-alpha 2a, rIFN-alpha 2b, rIFN-alpha 2a, consensus IFN alpha (infergen), feron, reaferon, intermax alpha, r-IFN-beta, infergen and actimmune, IFN-omega with DUROS, albuferon, locteron, Albuferon, Rebif, oral interferon alpha, IFNalpha-2b XL, AVI-005, PEG-Infergen, and pegylated IFN-beta.

Other targets for anti-HCV therapy under investigation include cyclophilin inhibitors which inhibit RNA binding to NS5b, nitazoxanide, Celgosivir (Migenix), an inhibitor of α-glucosidase-1, caspase inhibitors, Toll-like receptor agonists and immunostimulants such as Zadaxin (SciClone).

Ribavirin analogs and the ribavirin prodrug viramidine (taribavirin) have been administered with interferons to control HCV.

Commonly used abbreviations include: acetyl (Ac), aqueous (aq.), atmospheres (Atm), 2,2'-bis(diphenylphosphino)-1,1'-binaphthyl (BINAP), tert-butoxycarbonyl (Boc), di-tert-butyl pyrocarbonate or boc anhydride ($BOC_2O$), benzyl (Bn), butyl (Bu), Chemical Abstracts Registration Number (CASRN), benzyloxycarbonyl (CBZ or Z), carbonyl diimidazole (CDI), 1,5-diazabicyclo[4.3.0]non-5-ene (DBN), 1,8-diazabicyclo[5.4.0]undec-7-ene (DBU), N,N'-dicyclohexyl-carbodiimide (DCC), 1,2-dichloroethane (DCE), dichloromethane (DCM), diethyl azodicarboxylate (DEAD), di-iso-propylazodicarboxylate (DIAD), di-iso-butylaluminumhydride (DIBAL or DIBAL-H), di-iso-propylethylamine (DIPEA), N,N-dimethyl acetamide (DMA), 4-N,N-dimethylaminopyridine (DMAP), N,N-dimethylformamide (DMF), dimethyl sulfoxide (DMSO), 1-(3-dimethylaminopropyl)-3-ethylcarbodiimide hydrochloride (EDCI), ethyl (Et), ethyl acetate (EtOAc), ethanol (EtOH), 2-ethoxy-2H-quinoline-1-carboxylic acid ethyl ester (EEDQ), diethyl ether ($Et_2O$), O-(7-azabenzotriazole-1-yl)-N,N,N'N'-tetramethyluronium hexafluorophosphate acetic acid (HATU), acetic acid (HOAc), 1-N-hydroxybenzotriazole (HOBt), high pressure liquid chromatography (HPLC), iso-propanol (IPA), methanol (MeOH), melting point (mp), $MeSO_2$— (mesyl or Ms), methyl (Me), acetonitrile (MeCN), m-chloroperbenzoic acid (MCPBA), mass spectrum (ms), methyl tert-butyl ether (MTBE), N-methylmorpholine (NMM), N-methylpyrrolidone (NMP), phenyl (Ph), propyl (Pr), iso-propyl (i-Pr), pounds per square inch (psi), pyridine (pyr), room temperature (rt or RT), sat'd. (saturated), tert-butyldimethylsilyl or t-$BuMe_2Si$ (TBDMS), triethylamine (TEA or $Et_3N$), triflate or $CF_3SO_2$— (Tf), trifluoroacetic acid (TFA), O-benzotriazol-1-yl-N,N,N',N'-tetramethyluronium tetrafluoroborate (TBTU), thin layer chromatography (TLC), tetrahydrofuran (THF), tetramethylethylenediamine (TMEDA), trimethylsilyl or $Me_3Si$ (TMS), p-toluenesulfonic acid monohydrate (TsOH or pTsOH), 4-Me-$C_6H4SO_2$— or tosyl (Ts), N-urethane-N-carboxyanhydride (UNCA). Conventional nomenclature including the prefixes normal (n-), iso (i-), secondary (sec-), tertiary (tert-) and neo- have their customary meaning when used with an alkyl moiety. (J. Rigaudy and D. P. Klesney, Nomenclature in Organic Chemistry, IUPAC 1979 Pergamon Press, Oxford).

Compounds and Preparation

Examples of representative compounds encompassed by the present invention and within the scope of the invention are provided in TABLE I. These examples and preparations which follow are provided to enable those skilled in the art to more clearly understand and to practice the present invention. They should not be considered as limiting the scope of the invention, but merely as being illustrative and representative thereof. Compounds of the present invention can be made by a variety of methods depicted in the illustrative synthetic reaction schemes shown and described below. The starting materials and reagents used in preparing these compounds generally are either available from commercial suppliers, such as Aldrich Chemical Co., or are prepared by methods known to those skilled in the art following procedures set forth in references such as Fieser and Fieser's Reagents for Organic Synthesis; Wiley & Sons: New York, Volumes 1-21; R. C. LaRock, Comprehensive Organic Transformations, 2nd edition Wiley-VCH, New York 1999; Comprehensive Organic Synthesis, B. Trost and I. Fleming (Eds.) vol. 1-9 Pergamon, Oxford, 1991; Comprehensive Heterocyclic Chemistry, A. R. Katritzky and C. W. Rees (Eds) Pergamon, Oxford 1984, vol. 1-9; Comprehensive Heterocyclic Chemistry II, A. R. Katritzky and C. W. Rees (Eds) Pergamon, Oxford 1996, vol. 1-11; and Organic Reactions, Wiley & Sons: New York, 1991, Volumes 1-40. The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Some compounds in following schemes are depicted as a Markush structure with generalized substituents; however, one skilled in the art will immediately appreciate that the nature of the R groups as defined in the claims can varied as defined in the appended claims to afford the various compounds contemplated in this invention. Moreover, the reaction conditions are exemplary and alternative conditions can be identified without undue experimentation. The reaction sequences in the following examples are not meant to limit the scope of the invention as set forth in the claims.

In general, the nomenclature used in this Application is based on AUTONOM™ v.4.0, a Beilstein Institute computerized system for the generation of IUPAC systematic nomenclature. If there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it Examples of representative compounds encompassed by the present invention and within the scope of the invention are provided in the following Table. These examples and preparations which follow are provided to enable those skilled in the art to more clearly understand and to practice the present invention. They should not be considered as limiting the scope of the invention, but merely as being illustrative and representative thereof.

TABLE I

| | structure | MS (M + H) | MP | IC$_{50}$[1] (μmol) |
|---|---|---|---|---|
| I-1 | 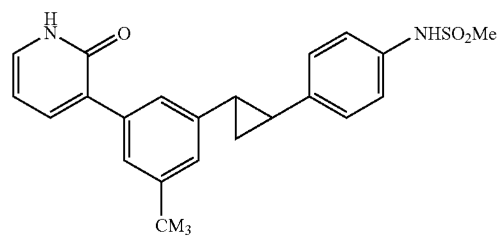 | 437 | 162.0-164.0 | 0.021 |
| I-2 | 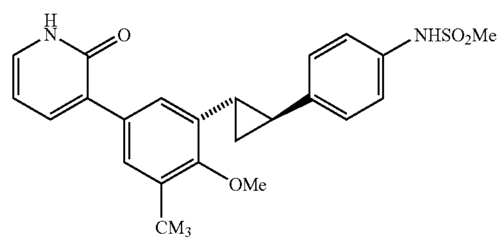 | 467 | | 0.0158 |
| I-3 | 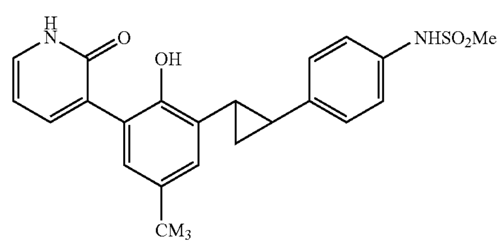 | 453 | 148.0-150.0 | 0.012 |
| I-4 | 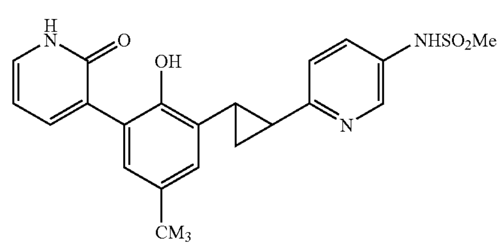 | 454 | 103-105 | 0.008 |
| I-5 | 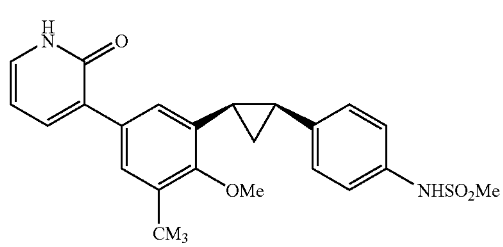 | 467 | | 0.75 |

1. IC50 HCV Polymerase Assay

The 1,2-diarylcyclopropanes encompassed by the present invention (e.g. A-7) can be prepared from A-2 which in turn is readily available from 3-tert-butyl-2-hydroxy-benzaldehyde (A-1a) by bromination of the 5-position with elemental bromine and subsequent alkylation of the phenol under basic conditions to afford A-2. Alkylation of phenol is typically carried out in solvents like DMF, THF, NMP, MeCN, acetone, DCM and DCE, at temperatures between 0° C. and 100° C. Typically used bases are $K_2CO_3$, sodium hydride, lithium hexamethyldisilazide, sodium hexamethyldisilazide and potassium hexamethyldisilazide. Alkylating agents such as alkyl halides, alkyl mesylates and alkyl triflates afford A-2.

catalysts include $Pd(PPh_3)_4$, $PdCl_2(dppf)$, $Pd(OAc)_2$ and $PdCl_2(PPh_3)_2$. With $PdCl_2(dppf)$, primary alkyl borane compounds can be coupled to aryl or vinyl halide or triflate without beta-elimination. The reaction can be carried out in a variety of organic solvents including toluene, THF, dioxane, DCE, DMF, DMSO and MeCN, aqueous solvents and under biphasic conditions. Reactions are typically run from about RT to about 150° C. Additives (e.g., CsF, KF, TlOH, NaOEt and KOH) frequently accelerate the coupling. Although there are numerous components in the Suzuki reaction such as the particular palladium catalyst, the ligand, additives, solvent, temperature, numerous protocols have been identified.

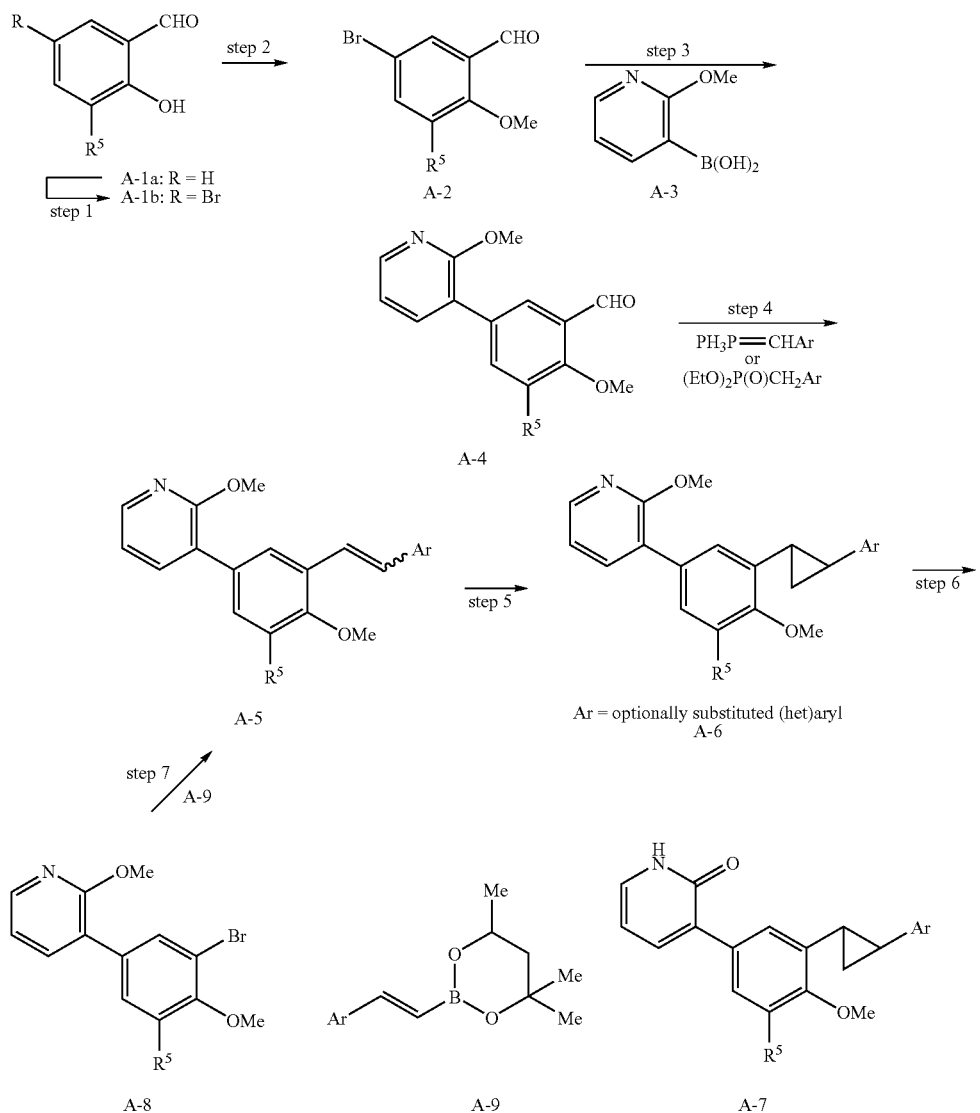

SCHEME A

Coupling of the latent pyridone (or other heteroaryl group within the scope of the invention) and the aryl ring is accomplished by Suzuki coupling. SCHEME A depicts the coupling of 2-methoxy-pyridin-3-yl boronic acid (A-3, step 3). Subsequent cleavage of the O-Me bond (step 6) affords the desired pyridone.

The Suzuki reaction is a palladium-catalyzed coupling of a boronic acid with an aryl or vinyl halide or triflate. Typical Highly active catalysts have been described (see, e.g., J. P. Wolfe et al., *J. Am. Chem. Soc.* 1999 121(41):9550-9561 and A. F. Littke et al., *J. Am. Chem. Soc.* 2000 122(17):4020-4028). In addition to 2-alkoxy-pyidinyl-3-boronic acids, the coupling can also be carried out with B-(1,2-dihydro-2-oxo-3-pyridinyl)-boronic acid, B-(1,2,3,4-tetrahydro-2,4-dioxo-5-pyrimidinyl)-boronic acid and B-(2,3-dihydro-3-oxo-4-pyridazinyl)-boronic acid. One skilled in the art will be able to identify a satisfactory protocol without undue experimentation.

The stilbene intermediates (e.g., A-5) are prepared from A-4 employing a Wittig homologation with benzyl-triphenyl-$\lambda^5$-phosphane or a substituted analog thereof (step 4). The Wittig reaction is the reaction of an aldehyde or ketone with a triphenyl phosphonium ylide to afford an alkene and triphenylphosphine oxide. (A. Maercker, *Org. React.* 1965, 14, 270-490; A. W. Carruthers, Some Modern Methods of Organic Synthesis, Cambridge University Press, Cambridge, UK, 1971, pp 81-90) Wittig reactions are most commonly used to condense aldehydes or ketones to singly substituted phosphine ylides. The Wittig reagent is usually prepared from a phosphonium salt, which is, in turn, prepared by alkylation of $Ph_3P$ with an alkyl halide. To form the Wittig reagent (ylide), the phosphonium salt is suspended in a solvent such as $Et_2O$ or THF and a strong base such as phenyl lithium or n-butyllithium is added. With simple ylides, the product is usually mainly the Z-isomer, although a lesser amount of the E-isomer also is often formed. This is particularly true when ketones are used. If the reaction is performed in DMF in the presence of LiI or NaI, the product is almost exclusively the Z-isomer. If the E-isomer is the desired product, the Schlosser modification may be used.

Alternatively The Horner-Wadsworth-Emmons reaction (B. E. Maryanoff and A. B. Reitz, *Chem. Rev.* 1989 89:863-927) produces predominantly E-alkenes. The Horner-Wadsworth-Emmons reaction (HWE reaction) is the condensation of stabilized phosphonate carbanions with aldehydes (or ketones). In contrast to phosphonium ylides used in the Wittig reaction, phosphonate-stabilized carbanions are more nucleophilic and more basic.

Compounds encompassed by the present invention wherein Ar is substituted can be prepared from benzyl ylides or diethyl benzylphosphonates which can be easily prepared from readily available benzyl halides. Sulfonamides encompassed within the scope of the claims are prepared by the HWE condensation of (4-nitro-benzyl)-phosphonic acid diethyl ester and A-4. Subsequent reduction of the nitro substituent affords an amine which can be concerted to a sulfonamide with mesyl chloride or with other readily available sulfonamides such as cycloalkylsulfonyl chlorides or haloalkylsulfonyl chlorides. Suitable reducing agents to convert the nitro group to the corresponding amine include, e.g., $LiAlH_4$, $LiBH_4$, Fe, Sn or Zn, in a reaction inert solvent, e.g. MeOH, EtOH, diglyme, benzene, toluene, xylene, o-dichlorobenzene, DCM, DCE, THF, dioxane, or mixtures thereof. If desired, when the reducing reagent is Fe, Sn or Zn, the reaction is carried out under acidic conditions in the presence of water. Sulfonylation or acylation of the resulting amine, if desired, is carried out by treating the amine with an activated carboxylic acid or a sulfonyl halide.

The cyclopropyl ring is introduced (step 5) by palladium acetate catalyzed cyclopropanation of A-5 with diazomethane. (R Paulssen et al., *Tetrahedron Lett.* 1972 1465; M. Suda et al., *Synthesis* 1981 714). The sequence of steps depicted in SCHEME A is not critical and one skilled in the art will understand that they can be altered to adapt to the individual compound being prepared and to the available synthetic intermediates.

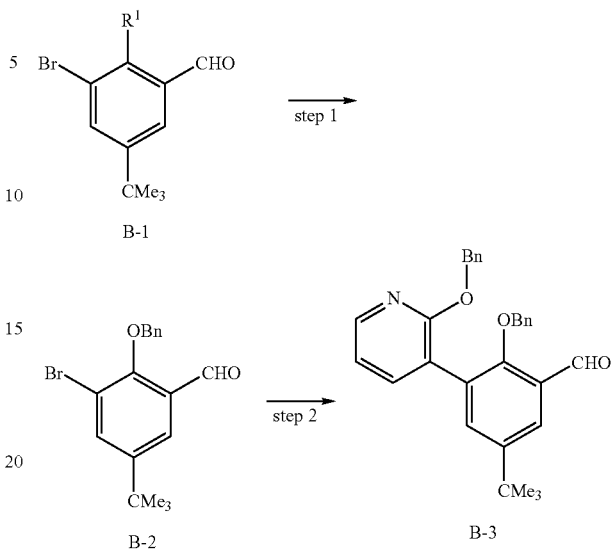

The preparation of compounds of the present invention substituted at the 2-position can be prepared by an analogous sequence starting with B-1. When $R^1$ is a hydroxyl group, the acidic phenol is conveniently protected as a benzyl ether. Incorporation of the latent pyridone as a benzyloxy-pyridine allows concomitant removal of the two benzyl ethers and reduction of the olefin. Alternatively, incorporation of the latent pyridone as a methoxy-pyridine permits stepwise debenzylation and demethylation (see e.g., example 7) One skilled in the art will appreciate other functional groups can be used if desired. Other compounds wherein $R^1$ is alkoxy or substituted alkoxy within the scope of the present invention can be prepared by alkylation of the phenol prior to step 2 with a suitable alkylating agent. Conversion of B-3 to the final product is carried out as depicted in SCHEME A.

Compounds of the present invention wherein $R^1$ is cyano can be from 4-tert-butyl-3,5 dibromo-aniline (CASRN 10546-67-5) wherein the cyano substituent is introduced by a Sandmeyer reaction. Sequential Suzuki couplings with A-3 (or another heteroaryl compound within the scope of the invention) and a appropriately substituted 4,4,6-trimethyl-2 ((E)-styryl)-[1,3,2]dioxaborinane A-9 (A. P. Lightfoot et al., *Tetrahedron Lett.* 2003 44:7645; *Synlett.* 2005 529; N. PraveenGanesh et al., *J. Org Chem.* 2007 72(12)4510) afford a stilbene derivative (SCHEME A-step 7) which can be carried on to a compound of present invention by procedures in SCHEME A.

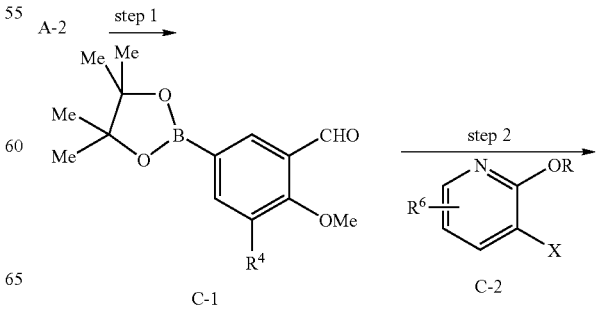

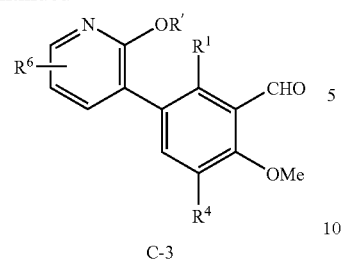

C-3

One skilled in the art will appreciate that the intermediate bearing the boronic acid (or boronic ester) and the leaving group can be interchanged. Thus, for example A-2 can be converted to a boronic acid (ester) C-1 and subjected to a Suzuki cross coupling with C-2 (a substituted 2-alkoxy-pyidine C-2 or a 3-halo-2-alkoxypyrazine wherein X is halo, trifluorosulfonyloxy or toluenesulfonyloxy) to afford C-3. The optimal route frequently is determined by the availability of the requisite starting materials.

SCHEME D

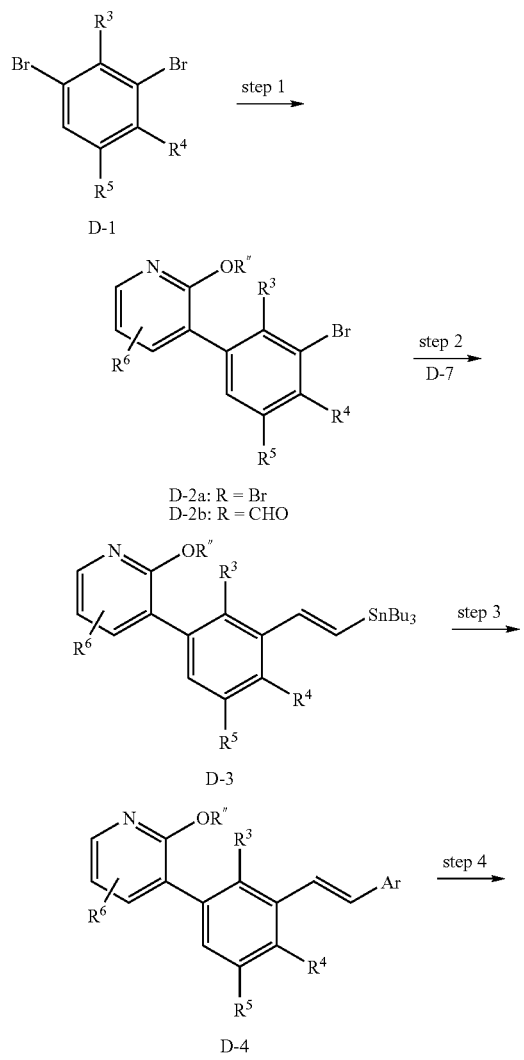

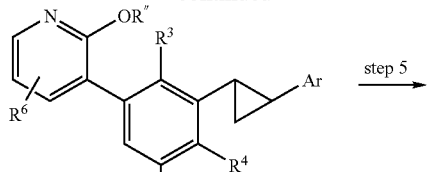

D-5

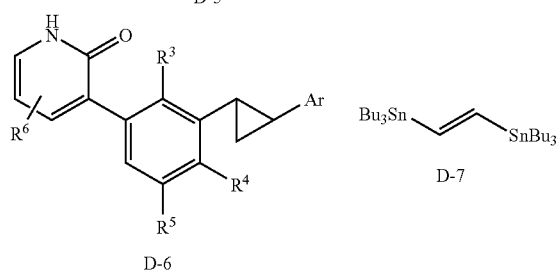

$R^1$ = H, —O-alkyl, —OCH$_2$Ph;
$R^3$ = H, O-alkyl
R″ = —OMe —OCH$_2$Ph;
Ar = optionally substituted (het)aryl An alternative route to 1,2-diarylcyclopropanes in the present invention utilizes a Stille palladium-catalyzed cross-couplings with 1-[dibutyl-((E)-2-tributylstannanyl-vinyl)-stannanyl]-butane (D-7) as depicted in SCHEME D. Coupling of D-1 and a pyridinyl-boronic acid under conditions described herein affords D-2a. Sequential Stille-type couplings with D-7 (step 2) initially afford D-3 which is subsequently coupled (step 4) with a substituted halo-(hetero)aryl compound such as 2-iodo-5-nitro-pyridine to afford the 1,2-diaryl-ethene D-4 which can converted to the corresponding cyclopropane. When the penultimate target is a sulfonamide the nitro group is reduced to the amine and sulfonylated using standard methodology. Alternatively the aldehyde can be converted to the corresponding acetylene (D-2, R=C≡H) and hydrostannylated as described in Example 3.

Other heteroaryl rings can be introduced by coupling with intermediates such as 6-bromo-pyridazin-3-ylamine (CASRN 88497-27-2), 2-bromo-5-nitro-pyrazine (CASRN 117103-53-4) and 2-amino-5-iodo-pyrimidine (CASRN 1445-39-2).

The Stille cross-coupling reaction is a palladium-catalyzed coupling of an aryl or vinyl stannanes with aryl or vinyl halides or -sulfonyloxy compounds (J. K. Stille *Angew. Chem. Int. Ed.* 1986 25:508-524; A. F. Littke and G. C. Fu, *Angew. Chem. Int. Ed.* 1999, 38:2411-2413). Commercially available Pd reagents including Pd(PPh$_3$)$_4$, Pd(OAc)$_2$ and Pd$_2$(dba)$_3$ can be used. Phosphine ligands are useful rate accelerants if they are not a component of the palladium catalyst. Relatively poorly electron-donating ligands tend to provide the greatest rate acceleration (V. Farina and B. Krishnan, *J. Am. Chem. Soc.* 1991 113:9585-9595). Additives including CuI have been incorporated to provide rate accelerations (V. Farina et al. *J. Org. Chem.* 1994 59:5905-5911). The reaction is typically run in aprotic solvents at elevated temperature.

Anti-Viral Activity

The activity of the inventive compounds as inhibitors of HCV activity may be measured by any of the suitable methods known to those skilled in the art, including in vivo and in vitro assays. For example, the HCV NS5B inhibitory activity of the compounds of formula I can determined using standard assay procedures described in Behrens et al., *EMBO J.* 1996 15:12-22, Lohmann et al., *Virology* 1998 249:108-118 and Ranjith-Kumar et al., *J. Virology* 2001 75:8615-8623. Unless otherwise noted, the compounds of this invention have demonstrated in vitro HCV NS5B inhibitory activity in such standard assays. The HCV polymerase assay conditions used for compounds of the present invention are described in Example 3. Cell-based replicon systems for HCV have been developed, in which the nonstructural proteins stably replicate subgenomic viral RNA in Huh7 cells (V. Lohmann et al., *Science* 1999 285:110 and K. J. Blight et al., *Science* 2000 290:1972. The cell-based replicon assay conditions used for compounds of the present invention are described in Example 4. In the absence of a purified, functional HCV replicase consisting of viral non-structural and host proteins, our understanding of Flaviviridae RNA synthesis comes from studies using active recombinant RNA-dependent RNA-polymerases and validation of these studies in the HCV replicon system. Inhibition of recombinant purified HCV polymerase with compounds in vitro biochemical assays may be validated using the replicon system whereby the polymerase exists within a replicase complex, associated with other viral and cellular polypeptides in appropriate stoichiometry. Demonstration of cell-based inhibition of HCV replication may be more predictive of in vivo function than demonstration of HCV NS5B inhibitory activity in vitro biochemical assays Dosage and Administration The compounds of the present invention may be formulated in a wide variety of oral administration dosage forms and carriers. Oral administration can be in the form of tablets, coated tablets, dragées, hard and soft gelatin capsules, solutions, emulsions, syrups, or suspensions. Compounds of the present invention are efficacious when administered by other routes of administration including continuous (intravenous drip) topical parenteral, intramuscular, intravenous, subcutaneous, transdermal (which may include a penetration enhancement agent), buccal, nasal, inhalation and suppository administration, among other routes of administration. The preferred manner of administration is generally oral using a convenient daily dosing regimen which can be adjusted according to the degree of affliction and the patient's response to the active ingredient.

A compound or compounds of the present invention, as well as their pharmaceutically useable salts, together with one or more conventional excipients, carriers, or diluents, may be placed into the form of pharmaceutical compositions and unit dosages. The pharmaceutical compositions and unit dosage forms may be comprised of conventional ingredients in conventional proportions, with or without additional active compounds or principles, and the unit dosage forms may contain any suitable effective amount of the active ingredient commensurate with the intended daily dosage range to be employed. The pharmaceutical compositions may be employed as solids, such as tablets or filled capsules, semi-solids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. A typical preparation will contain from about 5% to about 95% active compound or compounds (w/w). The term "preparation" or "dosage form" is intended to include both solid and liquid formulations of the active compound and one skilled in the art will appreciate that an active ingredient can exist in different preparations depending on the target organ or tissue and on the desired dose and pharmacokinetic parameters.

The term "excipient" as used herein refers to a compound that is useful in preparing a pharmaceutical composition, generally safe, non-toxic and neither biologically nor otherwise undesirable, and includes excipients that are acceptable for veterinary use as well as human pharmaceutical use. The compounds of this invention can be administered alone but will generally be administered in admixture with one or more suitable pharmaceutical excipients, diluents or carriers selected with regard to the intended route of administration and standard pharmaceutical practice.

"Pharmaceutically acceptable" means that which is useful in preparing a pharmaceutical composition that is generally safe, non-toxic, and neither biologically nor otherwise undesirable and includes that which is acceptable for human pharmaceutical use.

Solid form preparations include powders, tablets, pills, capsules, cachets, suppositories, and dispersible granules. A solid carrier may be one or more substances which may also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. Solid form preparations may contain, in addition to the active component, colorants, flavors, stabilizers, buffers, artificial and natural sweeteners, dispersants, thickeners, solubilizing agents, and the like.

Liquid formulations also are suitable for oral administration include liquid formulation including emulsions, syrups, elixirs, aqueous solutions, aqueous suspensions. These include solid form preparations which are intended to be converted to liquid form preparations shortly before use. Emulsions may be prepared in solutions, for example, in aqueous propylene glycol solutions or may contain emulsifying agents such as lecithin, sorbitan monooleate, or acacia. Aqueous solutions can be prepared by dissolving the active component in water and adding suitable colorants, flavors, stabilizing, and thickening agents. Aqueous suspensions can be prepared by dispersing the finely divided active component in water with viscous material, such as natural or synthetic gums, resins, methylcellulose, sodium carboxymethylcellulose, and other well known suspending agents.

The compounds of the present invention may be formulated for parenteral administration (e.g., by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, emulsifying or suspending, stabilizing and/or dispersing agents. Alternatively, the active ingredient may be in powder form, obtained by aseptic isolation of sterile solid or by lyophilisation from solution for constitution before use with a suitable vehicle, e.g., sterile, pyrogen-free water.

The compounds of the present invention may be formulated for topical administration to the epidermis as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also containing one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

The compounds of the present invention may be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the present invention may be formulated for vaginal administration. Pessaries, tampons, creams, gels, pastes, foams or sprays containing in addition to the active ingredient such carriers as are known in the art to be appropriate. The compounds of the present invention may be formulated for nasal administration. The solutions or suspensions are applied directly to the nasal cavity by conventional means, for example, with a dropper, pipette or spray. The formulations may be provided in a single or multidose form. In the latter case of a dropper or pipette, this may be achieved by the patient administering an appropriate, predetermined volume of the solution or suspension. In the case of a spray, this may be achieved for example by means of a metering atomizing spray pump.

The compounds of the present invention may be formulated for aerosol administration, particularly to the respiratory tract and including intranasal administration. The compound will generally have a small particle size for example of the order of five (5) microns or less. Such a particle size may be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol may conveniently also contain a surfactant such as lecithin. The dose of drug may be controlled by a metered valve. Alternatively the active ingredients may be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition may be presented in unit dose form for example in capsules or cartridges of e.g., gelatin or blister packs from which the powder may be administered by means of an inhaler.

When desired, formulations can be prepared with enteric coatings adapted for sustained or controlled release administration of the active ingredient. For example, the compounds of the present invention can be formulated in transdermal or subcutaneous drug delivery devices. These delivery systems are advantageous when sustained release of the compound is necessary and when patient compliance with a treatment regimen is crucial. Compounds in transdermal delivery systems are frequently attached to an skin-adhesive solid support. The compound of interest can also be combined with a penetration enhancer, e.g., Azone (1-dodecylaza-cycloheptan-2-one). Sustained release delivery systems are inserted subcutaneously into to the subdermal layer by surgery or injection. The subdermal implants encapsulate the compound in a lipid soluble membrane, e.g., silicone rubber, or a biodegradable polymer, e.g., polylactic acid.

Suitable formulations along with pharmaceutical carriers, diluents and excipients are described in *Remington: The Science and Practice of Pharmacy* 1995, edited by E. W. Martin, Mack Publishing Company, 19th edition, Easton, Pa. A skilled formulation scientist may modify the formulations within the teachings of the specification to provide numerous formulations for a particular route of administration without rendering the compositions of the present invention unstable or compromising their therapeutic activity.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

In embodiments of the invention, the active compound or a salt can be administered in combination with another antiviral agent such as ribavirin, a nucleoside HCV polymerase inhibitor, another HCV non-nucleoside polymerase inhibitor or HCV protease inhibitor. When the active compound or its derivative or salt are administered in combination with another antiviral agent the activity may be increased over the parent compound. When the treatment is combination therapy, such administration may be concurrent or sequential with respect to that of the nucleoside derivatives. "Concurrent administration" as used herein thus includes administration of the agents at the same time or at different times. Administration of two or more agents at the same time can be achieved by a single formulation containing two or more active ingredients or by substantially simultaneous administration of two or more dosage forms with a single active agent.

The term "therapeutically effective amount" as used herein means an amount required to reduce symptoms of the disease in an individual. The dose will be adjusted to the individual requirements in each particular case. That dosage can vary within wide limits depending upon numerous factors such as the severity of the disease to be treated, the age and general health condition of the patient, other medicaments with which the patient is being treated, the route and form of administration and the preferences and experience of the medical practitioner involved. For oral administration, a daily dosage of between about 0.01 and about 1000 mg/kg body weight per day should be appropriate in monotherapy and/or in combination therapy. A preferred daily dosage is between about 0.1 and about 500 mg/kg body weight, more preferred 0.1 and about 100 mg/kg body weight and most preferred 1.0 and about 10 mg/kg body weight per day. Thus, for administration to a 70 kg person, the dosage range would be about 7 mg to 0.7 g per day. The daily dosage can be administered as a single dosage or in divided dosages, typically between 1 and 5 dosages per day. Generally, treatment is initiated with smaller dosages which are less than the optimum dose of the compound. Thereafter, the dosage is increased by small increments until the optimum effect for the individual patient is reached. One of ordinary skill in treating diseases described herein will be able, without undue experimentation and in reliance on personal knowledge, experience and the disclosures of this application, to ascertain a therapeutically effective amount of the compounds of the present invention for a given disease and patient.

A therapeutically effective amount of a compound of the present invention, and optionally one or more additional antiviral agents, is an amount effective to reduce the viral load or achieve a sustained viral response to therapy. Useful indicators for a sustained response, in addition to the viral load include, but are not limited to liver fibrosis, elevation in serum transaminase levels and necroinflammatory activity in the liver. One common example, which is intended to be exemplary and not limiting, of a marker is serum alanine transminase (ALT) which is measured by standard clinical assays. In some embodiments of the invention an effective treatment regimen is one which reduces ALT levels to less than about 45 IU/mL serum.

The modification of the present compounds to render them more soluble in water or other vehicle, for example, may be easily accomplished by minor modifications (salt formulation, esterification, etc.), which are well within the ordinary skill in the art. It is also well within the ordinary skill of the art to modify the route of administration and dosage regimen of a particular compound in order to manage the pharmacokinetics of the present compounds for maximum beneficial effect in patients.

The following examples illustrate the preparation and biological evaluation of compounds within the scope of the invention. These examples and preparations which follow are provided to enable those skilled in the art to more clearly understand and to practice the present invention. They should not be considered as limiting the scope of the invention, but merely as being illustrative and representative thereof.

EXAMPLE 1

N-(4-{2-[3-tert-Butyl-5-(2-oxo-1,2-dihydro-pyridin-3-yl)-phenyl]-cyclopropyl}-phenyl)-methanesulfonamide (I-1)

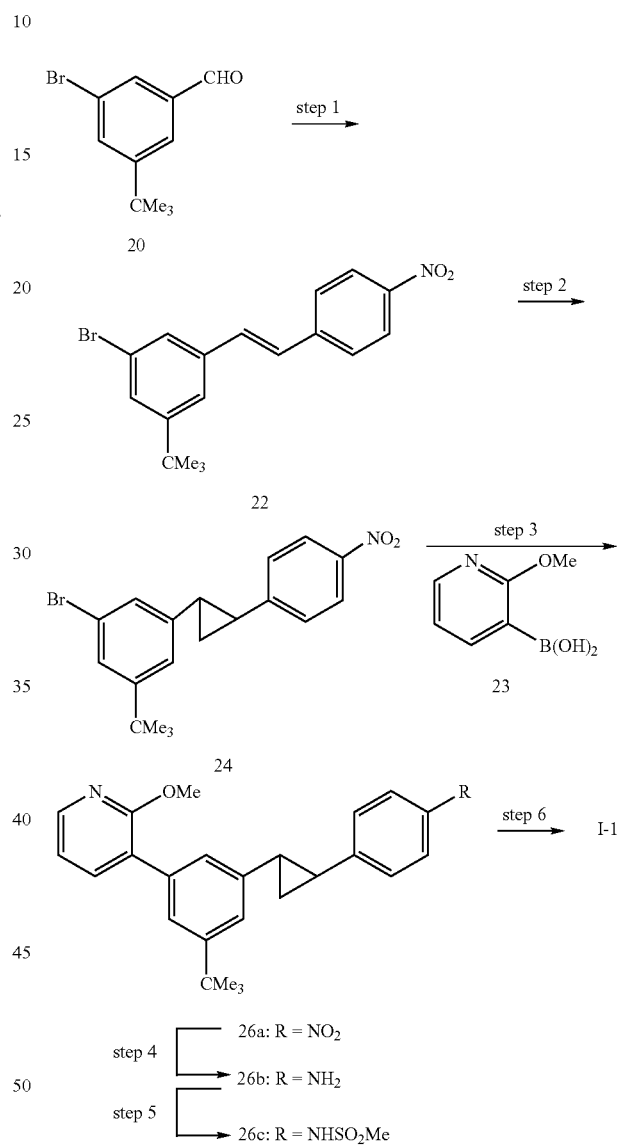

step 1—To a slurry of NaH (0.38 g, 9.46 mmol) and 15-crown-5 (0.17 g, 0.79 mmol) in THF (5 mL) cooled to 0° C. was added slowly a solution of diethyl (4-nitro-benzyl)-phosphonate (2.58 g, 9.46 mmol) and THF (8 mL). The resulting solution was stirred at 0° C. until the bubbling ceased. To the resulting solution maintained at 0° C. was added slowly a solution of 20 (1.90 g, 7.88 mmol) and THF (20 mL). The reaction was stirred at 0° C. for 20 min then quenched with $H_2O$. The solution was extracted with $Et_2O$ and the organic extracts washed with brine, dried ($Na_2SO_4$), filtered and evaporated. The crude product was purified by $SiO_2$ chromatography eluting with 10% EtOAc/hexane to afford 2.64 g of 22 as a yellow solid.

ethereal diazomethane solution—To a solution of KOH (4 g) in H₂O (10 mL) and Et₂O (40 mL) cooled to 0° C. was added portionwise N-nitroso-N-methyl urea (4 g). The resulting solution was stirred at 0° C. for 1 h then cooled to −78° C. and the upper layer consisting of an ethereal solution of diazomethane was used.

step 2—To a solution of 22 (1.0 g, 2.77 mmol), Pd(OAc)₂ (0.10 g) and DCM (10 mL) cooled to 0° C. was added dropwise an ethereal solution of diazomethane (10 equivalents). After bubbling ceased the reaction was quenched with HOAc (10 equivalents) and the resulting solution washed with sat'd. aq. NaHCO₃. The organic phase was dried (Na₂SO₄), filtered and evaporated. The crude product was purified by SiO₂ chromatography eluting with 10% EtOAc/hexane to afford 0.986 g of 24 as a yellow oil.

step 3—A microwave vial was charged with 24 (0.16 g, 0.427 mmol), 2-methoxy-pyridin-3-yl boronic acid (23, 0.13 g, 0.855 mmol), Na₂CO₃ (0.14 g, 1.22 mmol), Pd(PPh₃)₄ (0.1 g, 0.04 mmol) and a mixture of DCM and MeOH, sealed and irradiated in a microwave synthesizer at 115° C. for 35 min. The solution was cooled, filtered and concentrated in vacuo. The crude product was purified by SiO₂ chromatography eluting with an EtOAc/hexane gradient (0 to 10% EtOAc) to afford 0.14 g of 26a.

step 4—A suspension of 26a (0.14 g, 0.348 mmoL) and aqueous MeOH (6 mL 1:1) was heated at reflux. To the suspension was added NH₄Cl (0.19 g, 3.478 mmol) followed by Fe powder (0.10 g 1.739 mmol). The solution was heated at reflux for 2 h, cooled and filtered. The filtrate was concentrated in vacuo. The filtrate was taken up in EtOAc, sequentially washed with H₂O and brine, dried (Na₂SO₄), filtered and evaporated. The crude product was purified by SiO₂ chromatography eluting with 30% EtOAc/hexane to afford 0.10 g (77%) of 26b.

step 5—To a solution of 26b ((0.10 g, 0.268 mmol) in pyridine (3 mL) was added mesyl chloride (31 μL, 0402 mmol) and the resulting solution stirred for 1 h. The reaction mixture was diluted with EtOAc and washed sequentially with aqueous CuSO₄, 2N HCl and sat'd. NaHCO₃. The organic phase was dried (Na₂SO₄), filtered and concentrated in vacuo. The crude product was purified by SiO₂ chromatography eluting with an EtOAc/hexane gradient (20 to 50% EtOAc) to afford 0.14 g of 26c.

step 6—A solution of 26c (0.14 g, 0.30 mmol), HOAc (3 mL) and HBr (105 μL) was heated ar 50° C. for 2 d. The reaction mixture was cooled to RT, diluted with EtOAc and washed sequentially with H₂O and sat'd. NaHCO₃. The organic phase was dried (Na₂SO₄), filtered and concentrated in vacuo. The crude product was purified by SiO₂ chromatography eluting with a gradient of DCM and a solution of DCM/MeOH/NH₄OH (60:10:1) (70 to 20% DCM) to afford 80 mg of I-1.

EXAMPLE 2

N-(4-{2-[3-tert-Butyl-2-methoxy-5-(2-oxo-1,2-dihydro-pyridin-3-yl)-phenyl]-cyclopropyl}-phenyl)-methanesulfonamide (I-2)

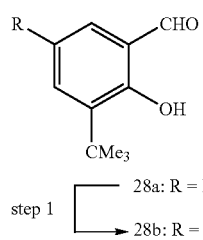

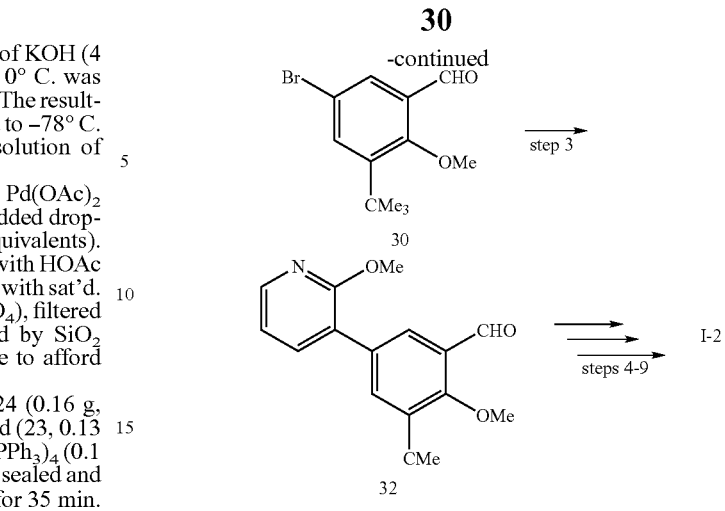

step 1—To a solution of 28a (5.00 g, CASRN 24623-65-2) and DCM (20 mL) at 0° C. was added dropwise a solution of Br₂ (1.45 mL) in DCM (15 mL) over a period of 30 min. After the addition was complete the reaction was stirred for 1 h before the organic volatiles were removed under reduced pressure to afford 7.23 g of 28b as a light yellowish solid.

step 2—A mixture of 28b (3.83 g), MeI (2.32 mL) and K₂CO₃ (6.18 g) in DMF (50 mL) was heated at 50° C. for 1 h then cooled to RT and diluted with ether and water. The organic layer was thrice washed with water then brine, dried (MgSO₄) and concentrated to afford 3.99 g of 30 as a yellow solid.

step 3—A sealed tube containing 30 (1.08 g), 23 (0.91 g), Na₂CO₃ (1.05 g) and Pd(PPh₃)₄ (460 mg) in a mixture of MeOH (20 mL) and DCM (5 mL) was irradiated in a microwave reactor at 120° C. for 30 min. The organic volatiles were removed under reduced pressure. The residue was partitioned between EtOAc and water. The organic layer was washed with brine, dried (Na₂SO₄), filtered and concentrated. The crude residue was purified by SiO₂ chromatography eluting with an EtOAc/hexane gradient (0 to 20% EtOAc) to afford 300 mg of 32.

The conversion of 32 to I-2 (steps 4-9) was carried out in accord with the procedures described in steps 1-6 of example 1 to afford I-2 as a mixture of cis and trans isomers.

EXAMPLE 3

N-(6-{2-[3-tert-Butyl-6-hydroxy-2-methoxy-5-(2-oxo-1,2-dihydro-pyridin-3-yl)-phenyl]-cyclopropyl}-pyridin-3-yl)-methanesulfonamide (I-4)

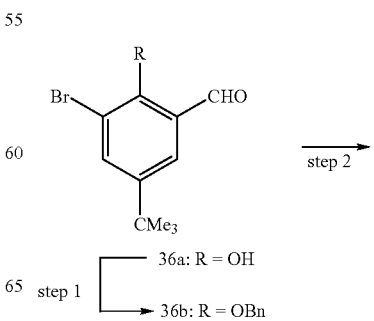

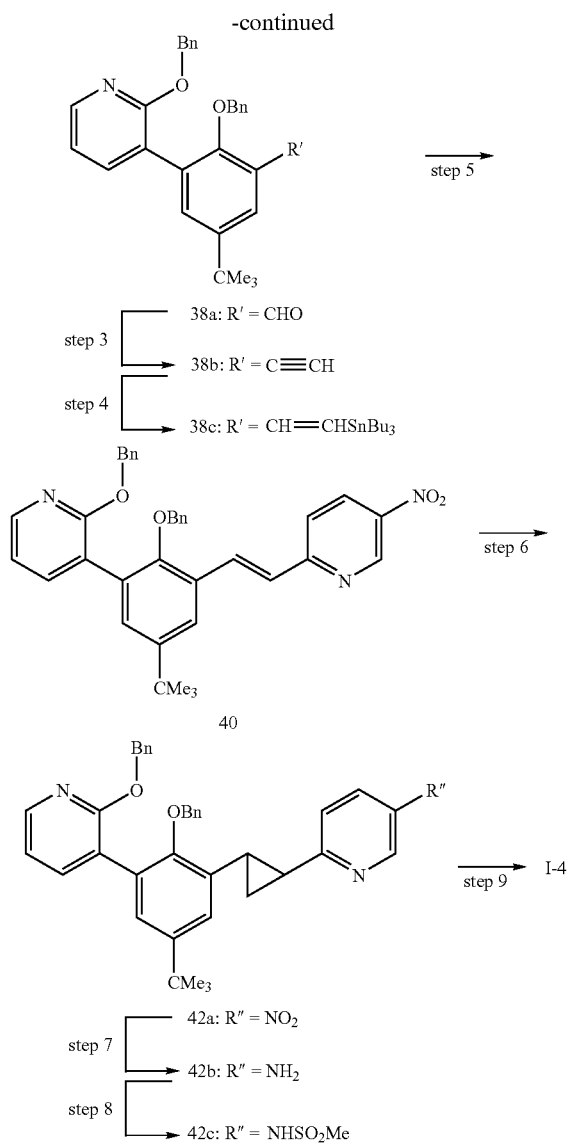

2-benzyloxy-pyridin-3-ylboronic acid (34)—A solution of 2-benzyloxy-3-bromo-pyridine (2.50 g, 9.47 mmol), Pd(II)Cl$_2$(PPh$_3$)$_2$ (232 mg, 0.28 mmol), KOAc (2.32 g, 23.67 mmol), bis-(pinacolato)diborane (2.95 g, 11.36 mmol) and DME (75 mL) was heated at 70° C. for 26 h. The reaction mixture was cooled and partitioned between Et$_2$O and water. The organic phase was separated, dried and evaporated. The crude product was purified by SiO$_2$ chromatography eluting with a EtOAc/hexane gradient (0 to 5% EtOAc to afford 1.81 g of 34 containing a small amount of bis-(pinacolato)diborane.

step 1—Benzylation of 3-bromo-5-tert-butyl-2-hydroxy benzaldehyde (36a) with benzyl bromide is accomplished treating 36a with benzyl bromide and tetrabutylammonium hydroxide in a biphasic system comprised of MeOH and DCM to afford 2-benzyloxy-3-bromo-5-tert-butyl-benzaldehyde (36b).

step 2—A microwave vial was charged with 36b (1.5 g, 4.31 mmol), 34 (1.28 g, 5.60 mmol), Pd(PPh$_3$)$_4$ (0.5 g, 0.43 mmol) and Na$_2$CO$_3$ (1.37 g, 12.93 mmol) and flushed with argon. To the tube was added MeOH (2.5 mL) and DCM (7.5 mL) and the tube was sealed and heated to 120° C. for 35 min. The reaction mixture was cooled to RT, filtered and concentrated in vacuo. The crude product was purified by SiO$_2$ chromatography eluting with 5% EtOAc/hexane to afford of 38a.

step 3—To a solution of 38a (1.11 g, 2.46 mmol) in MeOH (20 mL) cooled to −78° C., was added a solution of sodium methoxide (0.5M in MeOH, 9.84 mL, 4.92 mmol) followed by dropwise addition of a solution of dimethyl 1-diazo-2-oxopropylphoshonate (610 mg, 4.92 mmol) in MeOH (5 mL). The resulting reaction mixture was gradually warmed to RT and stirred overnight then quenched with a saturated aqueous NaHCO$_3$. The organic volatiles were removed under reduced pressure. The crude residue was partitioned between EtOAc and saturated aqueous NaHCO$_3$. The organic layer was washed with water, brine, and dried (Na$_2$SO$_4$), filtered and concentrated. The crude residue was purified by SiO$_2$ chromatography eluting with 5% EtOAc/hexane to afford 38b.

step 4—A round-bottom flask was charged with 38b (2 g, 4.47 mmol), AIBN (0.29 g) and benzene (20 mL) then flushed with argon then tributyl tin hydride (1.56 mL, 5.81 mmol) was added. The reaction mixture was heated at reflux for 3 h, cooled and concentrated in vacuo. The crude product was purified by SiO$_2$ chromatography eluting with 5% EtOAc/hexane to afford 38c.

step 5—To a solution of Pd$_2$(dba)$_3$ (0.104 g, 0.11 mmol) and DMF (10 mL) maintained under an Ar atmosphere was added tris-(2-furyl)phosphine (0.106 g, 0.45 mmol). After stirring the solution for 10 min the solution was added to a solution of 38c (2.8 g, 3.79 mmol), 2-iodo-5-nitro-pyridine (1.14 g, 4.55 mmol), LiCl (0.329 g, 7.58 mmol) and DMF (10 mL) which was maintained under an Ar atmosphere. The resulting solution was heated at 90° C. overnight, cooled, then partitioned between EtOAc and aq. NH$_4$Cl. The aqueous phase was extracted with EtOAc and the combined organic extracts were dried, filtered and concentrated in vacuo. The crude product was purified by SiO$_2$ chromatography eluting with an EtOAc/hexane gradient (5 to 10% EtOAc) to afford 40.

step 6—The cyclopropanation of 40 was carried out in accord with the procedure described in step 2 of example 1. The crude product was purified by SiO$_2$ chromatography eluting with a 5% EtOAc/hexane gradient to afford 42a.

step 7—To a solution of 42a (0.080 g) in EtOH (3.0 mL) was added Rainy-nickel (ca. 0.3 mL of a aqueous slurry) and the resulting solution stirred under an H$_2$ atmosphere (H$_2$ balloon) for 1 h. The solution was filtered and the filtrate concentrated in vacuo and purified on a SiO$_2$ column eluting with 40% EtOAc/hexane to afford 42b.

step 8—Conversion of 42b to the methanesulfonamide 42c was carried out in accord with the procedure described in step 5 of example 1.

step 9—Conversion of 42c to I-4 was carried out in accord with the procedure described in step 6 of example 1. The reaction was heated at 65° C. overnight. The crude product was purified on a preparative SiO$_2$ TLC plate developed with 10% MeOH/DCM to afford I-4.

The utilization of the Stille coupling to incorporate a pyridine ring as depicted in example 3 can be adapted to introduction of a pyrazine, pyridazine or pyrimidine ring.

EXAMPLE 4

N-(4-{2-[5-tert-Butyl-2-hydroxy-3-(2-oxo-1,2-dihydro-pyridin-3-yl)-phenyl]-cyclopropyl}-phenyl)-methanesulfonamide (I-3)

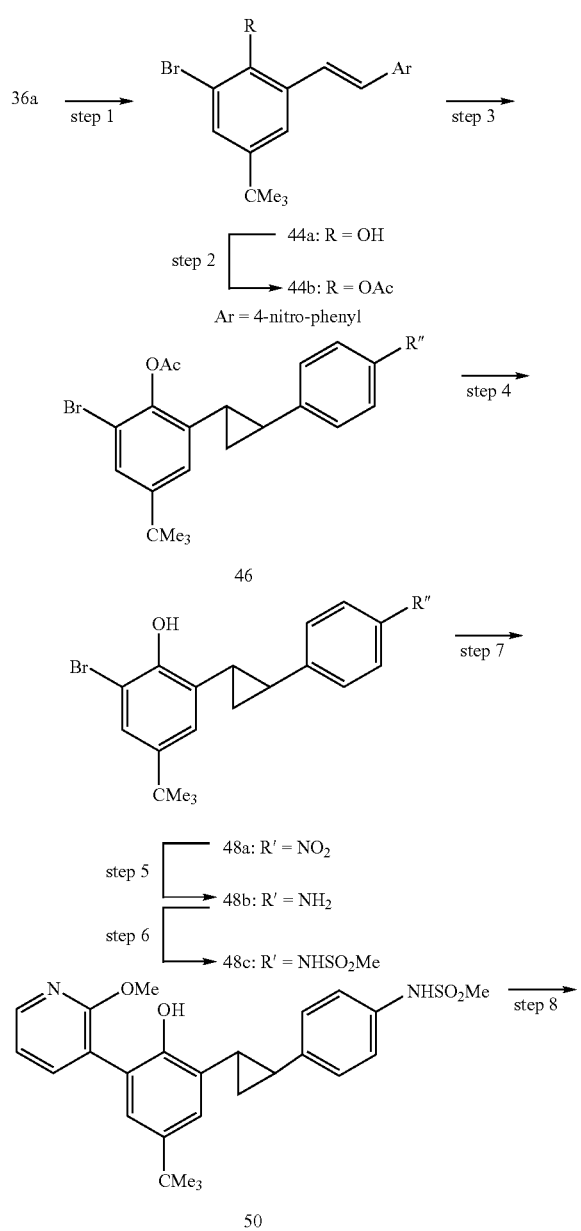

step 1 —To a solution of 15-crown-5 in THF (20 mL) cooled to 0° C. was added NaH (1.56 g, 3.9 mmol, 60% mineral oil dispersion) followed by a solution of diethyl (4-nitro-benzyl)-phosphonate (10.65 g, 3.9 mmol) and THF (20 mL). After stirring for 10 min a solution of 36a (5.0 g, 19.5 mmol) was added slowly. After 10 min at 0° C. the reaction was warmed to RT then heated at reflux for 6 h. The reaction was cooled to RT then quenched with 1N HCl and the resulting solution was extracted with EtOAc. The combined extracts were dried, filtered and evaporated. The crude product was purified by SiO$_2$ chromatography eluting with 5% EtOAc/hexane to afford 44a in a 65% yield.

step 2—To a solution of 44a (0.460 g, 1.22 mmol) and AcCl (96.3 μL, 1.35 mmol) in DCM (10 mL) cooled to 0° C. was added dropwise TEA (220 μL, 1.3 equivalents). After 2 h at RT the reaction mixture was partitioned between 1N HCl and EtOAc. The aqueous phase was extracted with EtOAc and the combined EtOAc extracts were dried, filtered and concentrated in vacuo. The crude product was purified by SiO$_2$ chromatography eluting with 5% EtOAc/hexane to afford 44b.

step 3—The cyclopropanation of 44b was carried out in accord with the procedure described in step 2 of example 1. The crude product was purified by SiO$_2$ chromatography eluting with a 5% EtOAc/hexane gradient to afford 46.

step 4 —To a solution of 46 (0.370 g) in MeOH (2.0 mL) and THF (2.0 mL) was added 2N NaOH (2.0 mL). After stirring for 1 h at RT the reaction was poured into 1N HCl and the resulting solution extracted with EtOAc. The combined extracts were dried, filtered and concentrated in vacuo. The crude product was purified by SiO$_2$ chromatography eluting with 5% EtOAc/hexane to afford 48a.

step 5—To a solution of 48a (0.340 g, 0.87 mmol) in EtOAc (10 mL) was added SnCl$_2$.2H$_2$O (0.98 g, 4.37 mmol). The resulting solution was heated at reflux for 2.5 h than cooled and poured into sat'd. aq. NaHCO$_3$. The resulting solution was extracted with EtOAc and the combined extracts dried, filtered and concentrated in vacuo. The crude product was purified by SiO$_2$ chromatography eluting with 30% EtOAc/hexane to afford 48b.

step 6—The conversion of 48b to the methanesulfonamide 48c was carried out in accord with the procedure described in step 5 of example 1.

step 7—The conversion of 48c to 50 was carried out in accord with the procedure described in step 3 of example 1. The crude product was purified by SiO$_2$ chromatography eluting with 30% EtOAc/hexane.

step 8—The conversion of 50 to I-3 was carried out in accord with the procedure described in step 6 of example 1. The crude product was purified by on a preparative SiO$_2$ TLC plate developed with 70% EtOAc/hexane followed by 5% MeOH/DCM.

Example 5

N-(4-{2-[3-tert-Butyl-5-(3-oxo-2,3-dihydro-pyridazin-4-yl)-phenyl]-cyclopropyl}-phenyl)-methanesulfonamide (56c)

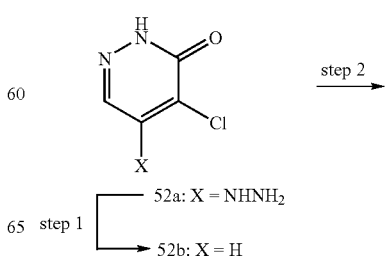

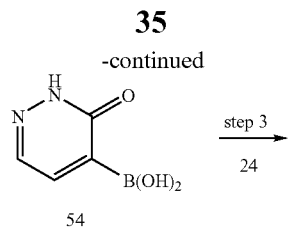

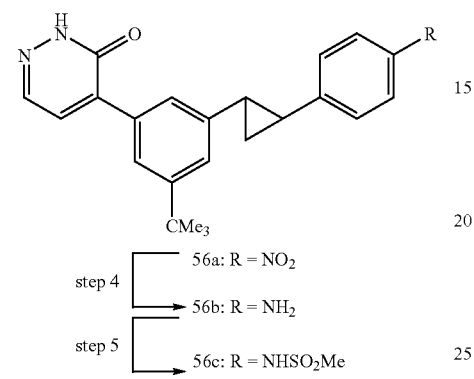

B-(2,3-dihydro-3-oxo-4-pyridazinyl)-boronic acid (52b)—A 1 L round-bottom flask was charged with 4-chloro-5-hydrazinyl-3(2H)-pyridazinone (52a, 8.0 g, 50 mmol), CuSO₄.5H₂O (26.12 g, 10.5 mmol) and H₂O (300 mL) and the mixture was stirred and heated at reflux overnight. The reaction was cooled to 0° C. and an aq. solution of NaOH was added until the pH was 4. The aqueous layer was thrice extracted with EtOAc (500 mL each). The combined extracts were dried (Na₂SO₄), filtered and evaporated. The remaining aqueous phase was adjusted to pH of 2 with 37% HCl and the solution extracted six times with EtOAc. The extracts were combined, dried (Na₂SO₄), filtered and evaporated to afford 4.75 g of 4-chloro-2H-pyridazin-3-one (52b)

step 2—A microwave vial was charged with 52b (0.400 g, 3 mmol), bis-(pinacolato)diboron (0.934 g, 4 mmol), dicyclohexyl[2',4',6'-tris(1-methylethyl)[1,1'-biphenyl]-2-yl]-phosphine (X-Phos, 0.058 g, 0.12 mmol), Pd₂(dba)₃ (0.056 g, 0.061 mmol) and KOAc (0.902 g, 9 mmol) and the flask was evacuated and back-filled with Ar and sealed. Dioxane (6 mL) was added and the reaction heated at 110° C. overnight. The reaction mixture was cooled to RT and extracted with EtOAc (120 mL). The organic extract was washed sequentially with H₂O (10 mL) and brine (10 mL), dried (Na₂SO₄), filtered and evaporated. The crude product was triturated with Et₂O to afford 0.217 g of 54.

step 3—A microwave vial is charged with 24, 54 (2 equivalents), Na₂CO₃ (2.8 equivalents), Pd(PPh₃)₄ (0.01 equivalents) and a mixture of DCM and MeOH, is sealed and is irradiated in a microwave synthesizer at 115° C. for 35 min. The solution is cooled, then filtered and concentrated in vacuo. The crude product is purified by SiO₂ chromatography eluting with an EtOAc/hexane gradient to afford of 56a.

Reduction of the nitro group and sulfonylation of the resulting amine is carried out in accord with the procedures described in steps 4 and 5 of Example 1 to afford 56c.

N-(4-{2-[5-tert-Butyl-2-hydroxy-3-(3-oxo-2,3-dihydro-pyridazin-4-yl)-phenyl]-cyclopropyl}-phenyl)-methanesulfonamide (58) is prepared by Suzuki coupling of 54 and 48c in accord with the procedure described in step 3 of the present example.

Example 6

N-(4-{2-[3-tert-Butyl-5-(2,4-dioxo-1,2,3,4-tetrahydro-pyrimidin-5-yl)-phenyl]-cyclopropyl}-phenyl)-methanesulfonamide (60)

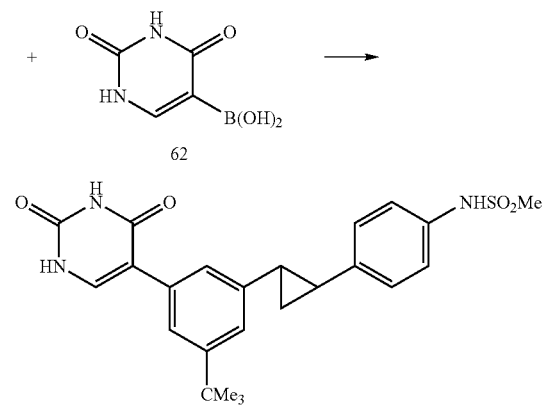

The title compound (60) is prepared by Suzuki coupling of 24 and 62 (CASRN 70523-22-7) in accord with the procedure described in step 3 of Example 1.

EXAMPLE 7

N-(4-{2-[3-tert-Butyl-2-methoxy-5-(3-oxo-3,4-dihydro-pyrazin-2-yl)-phenyl]-cyclopropyl}-phenyl)-methanesulfonamide (74)

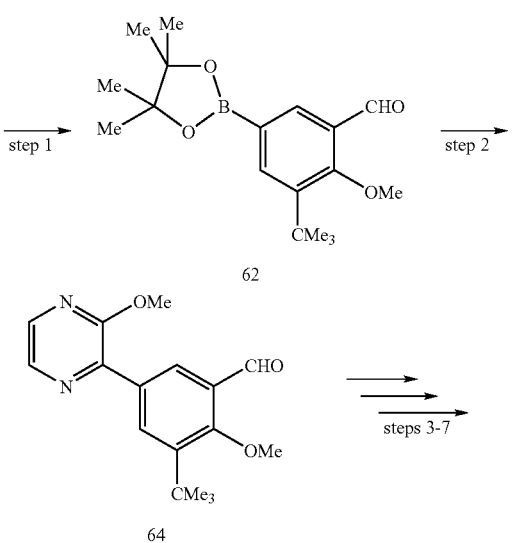

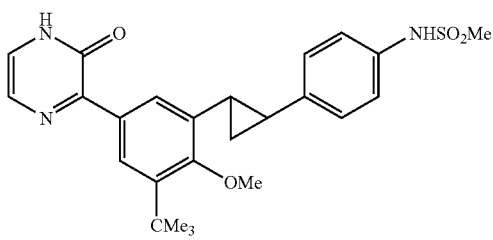

68 step 1—A mixture 30 (0.60 g CASRN 417715-878), bis-(pinacolato)diboron (31, 0.69 g), Pd(dppf)$_2$Cl$_2$ (54 mg) and KOAc (542 mg) in DME (30 mL) under an argon atmosphere was heated at 70° C. for 14 h and then at 90° C. for additional 7 h. The reaction was cooled to RT, and diluted with water and ether. The organic layer was washed with brine, dried (MgSO$_4$), filtered and concentrated. The crude residue was purified by SiO$_2$ chromatography eluting with a EtOAc/hexane gradient (0 to 12% EtOAc) to afford 478 mg of 62 contaminated with a small amount of 31.

step 2—A vial was charged with 62 (0.365 g 1.48 mmol), 2-chloro-3-methoxy-pyrazine (0.198 g, 1.370 mmol), Pd(Ph$_3$)$_4$ (0.106 g, 0.092 mmol) Na$_2$CO$_3$ (0.313 g, 2.953 mmol), MeOH (6 mL) and DCM (2 mL), sealed and irradiated in a microwave synthesizer at 115° C. for 30 min. The reaction mixture was cooled to RT, diluted with EtOAc, washed with brine, dried (Na$_2$SO$_4$), filtered and concentrated in vacuo. The crude product was purified by SiO$_2$ chromatography eluting with a EtOAc/hexane gradient (2 to 10% EtOAc) to afford 0.275 g of 64.

step 3—To a solution of 4-nitro-benzylphosphonium bromide (1.23 g, 2.573 mmol) and DMF (10 mL) cooled to 0° C. was added NaH (0.211 g, 5.275 mmol, 60% mineral oil dispersion). The solution was stirred for 30 min then a solution of 64 (0.251 g, 0.857 mmol) and DMF (5 mL) was added and the resulting solution stirred overnight at RT. The reaction was quenched by addition of 1N HCl (8 mL) and the resulting solution diluted with EtOAc. The EtOAc solution was separated and twice washed with brine, dried (Na$_2$SO$_4$), filtered and concentrated in vacuo. The crude product was purified by SiO$_2$ chromatography eluting with a EtOAc/hexane gradient (5 to 10% EtOAc) to afford 317 mg of 2-{3-tert-Butyl-4-methoxy-5-[(E)-2-(4-nitro-phenyl)-vinyl]-phenyl}-3-methoxy-pyrazine (66a).

Conversion of 66a into 2-{3-tert-butyl-4-methoxy-5-[2-(4-nitro-phenyl)-cyclopropyl]-phenyl}-3-methoxy-pyrazine (66b, step 4) is carried out with diazomethane and Pd(OAc)$_2$ in accord with step 2 of example 1

Reduction of the amine (step 5), conversion of the amine to the methanesulfonamide (step 6) is carried out in accord with steps 4 and 5 of example 1 to afford N-(4-{2-[3-tert-butyl-2-methoxy-5-(3-methoxy-pyrazin-2-yl)-phenyl]-cyclopropyl}-phenyl)-methanesulfonamide (66c).

Conversion of 66c to the title compound (step 7) is carried out in accord with step 6 of example 1.

EXAMPLE 8

N-(4-{2-[2-Methoxy-3-(1-methyl-cyclopropyl)-5-(2-oxo-1,2-dihydro-pyridin-3-yl)-phenyl]-cyclopropyl}-phenyl)-methanesulfonamide (78)

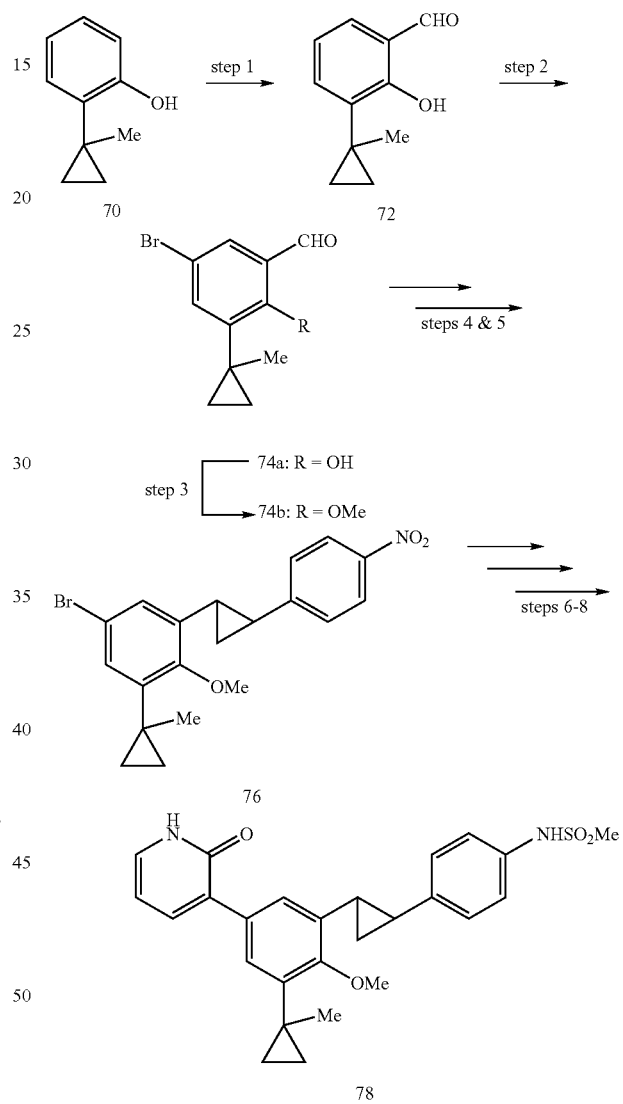

step 1—To a solution of 2-(1-methylcyclopropyl)phenol (70, 0.55 g, 3.4 mmol; CASRN 433684-77-6) in MeCN (7 mL) was added paraformaldehyde (0.68 g, 23 mmol), MgCl$_2$ (0.48 g, 0.051 mmol) and TEA (1.3 g, 13 mmol). The mixture was stirred and heated at reflux for 5 h. After cooling to RT, the reaction mixture was partitioned between DCM and 1M aqueous HCl, and the organic extracts were dried (Na$_2$SO$_4$), filtered and concentrated. The crude residue was purified by SiO$_2$ chromatography eluting with EtOAc/hexane to afford 0.34 g (58%) of 2-hydroxy-3-(1-methylcyclopropyl)-benzaldehyde (72) as a light yellow oil.

step 2: To a solution 72 (0.34 g, 1.9 mmol) in DCM-MeOH (3:2, 20 mL) was added tetrabutylammonium tribromide (0.98 g, 2.0 mmol) and the resulting mixture was stirred at RT for 75 min. The solvent was removed under reduced pressure and the residue was partitioned between EtOAc and water. The EtOAc layer was washed sequentially with water and brine, dried ($Na_2SO_4$), filtered and concentrated. The crude residue was purified by $SiO_2$ chromatography eluting with EtOAc/hexane to afford 0.45 g (91%) of 5-bromo-2-hydroxy-3-(1-methylcyclopropyl)benzaldehyde (74a) as a light yellow solid.

step 3—To a solution of 74a (0.44 g, 1.7 mmol) in DMF (4 mL) was added $K_2CO_3$ (0.60 g, 4.4 mmol) and iodomethane (0.32 g, 2.3 mmol). The resulting mixture was stirred at 60° C. for 2 h. The reaction mixture was cooled to RT and partitioned between water and $Et_2O$. The organic layer was washed sequentially with water and brine, dried ($Na_2SO_4$), filtered and concentrated to afford 0.47 g (96%) of 5-bromo-2-methoxy-3-(1-methylcyclopropyl)benzaldehyde (74b) as a light yellow solid.

step 4: Sodium hydride (60% dispersion, 0.10 g, 2.6 mmol) and 15-crown-5 (0.038 g, 0.17 mmol) were added to THF (5 mL) at 0° C. and stirred for 5 min. To the reaction mixture was then added dropwise over 5 min a solution of diethyl (4-nitrobenzyl)phosphonate (0.52 g, 1.9 mmol) in THF (5 mL), and stirring was continued at 0° C. for 5 min. To this reaction mixture was then added dropwise over 10 min a solution of 74b (0.47 g, 1.7 mmol) in THF (10 mL). The reaction mixture was stirred for 30 min at 0° C. then for 90 min at RT. Water was carefully added, and the mixture was partitioned between water and EtOAc. The EtOAc layer was washed sequentially with water and brine, dried ($Na_2SO_4$), filtered and concentrated. The crude residue was purified by $SiO_2$ chromatography eluting with EtOAc/hexane to afford 0.67 g (94%) of 5-bromo-2-methoxy-1-(1-methylcyclopropyl)-3-[(E)-2-(4-nitrophenyl)vinyl]benzene (75) as a yellow solid (0.67 g, 94%).

step 5—Introduction of the cyclopropyl group to afford 5-bromo-2-methoxy-1-(1-methyl-cyclopropyl)-3-[(E)-2-(4-nitro-phenyl)-vinyl]-benzene (76) is carried out in accord with the procedure described in step 2 of example 1.

Preparation of 2-oxo-1,2-dihydropyridine-3-boronic acid (80)—To a solution of 3-bromo-2-oxo-1,2-dihydropyridine (3.3 g, 19 mmol) in THF (200 mL) cooled to −76° C. was added dropwise over 15 min TMEDA (6.5 g, 56 mmol), followed by n-butyllithium (2.5M in hexane, 58 mmol). The resulting mixture was stirred for 15 min at −76° C. and then warmed to RT. Upon reaching an internal temperature of 19° C., the reaction mixture was cooled to 0° C., and $B(OMe)_3$ (4.0 g, 39 mmol) was added dropwise over 15 min. After the addition was complete, the reaction mixture was warmed to RT and was stirred for 15 h. The mixture was then cooled to 0° C. and a small amount of ice was added followed by 2M aqueous HCl (100 mL). The THF was removed under reduced pressure, and the aqueous solution was washed twice with DCM. Concentrated aqueous NaOH was added slowly until pH 5 was attained and a precipitate formed. The mixture was cooled to 0° C. and stirred for 10 min. The solid was collected by filtration, washed with cold water, and dried under vacuum to afford 1.83 g (69%) of 80 as a yellow solid.

Reduction of the amine (step 6), conversion of the amine to the methanesulfonamide (step 7) is carried out in accord with steps 4 and 5 of example 1 to afford N-(4-{2-[5-bromo-2-methoxy-3-(1-methyl-cyclopropyl)-phenyl]-cyclopropyl}-phenyl)-methanesulfonamide (66c). Palladium-catalyzed cross-coupling of 80 and 66c to the title compound (step 8) is carried out in accord with step 3 of example 1 to afford the title compound.

EXAMPLE 9

N-(4-{(E)-2-[3,3-Dimethyl-7-(3-oxo-2,3-dihydro-pyridazin-4-yl)-2,3-dihydro-benzofuran-5-yl]-vinyl}-phenyl)-methanesulfonamide (100)

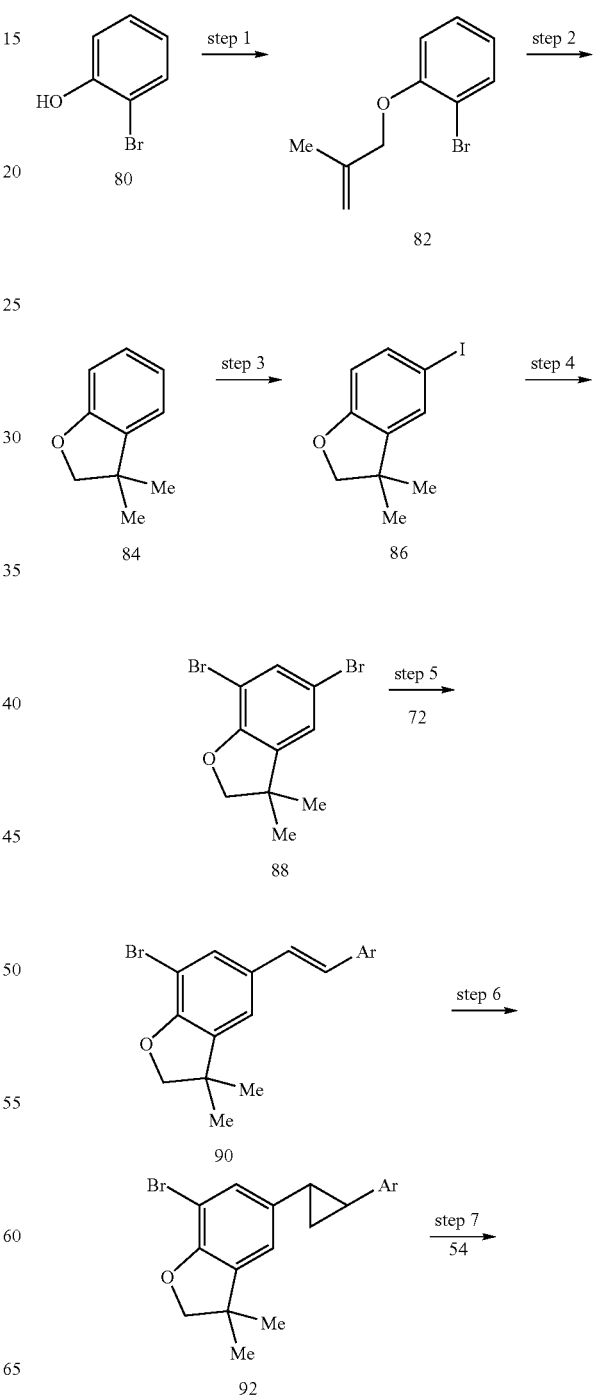

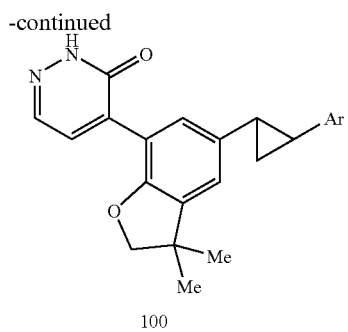

Ar = 4-methanesulfonylamino-phenyl step 1—To a solution of 80 (2.457 g, 14 mmol) and acetone (75 mL) was added K$_2$CO$_3$ (4.907 g, 36 mmol) and 3-bromo-2-methyl propene (2.0 mL, 20 mmol) and the resulting solution was heated at reflux overnight. The reaction mixture was cooled and concentrated in vacuo. The residue was partitioned between EtOAc (150 mL) and H$_2$O (40 mL). The aqueous phase was extracted with EtOAc and the combined organic extracts were sequentially washed with H$_2$O and brine, dried (Na$_2$SO$_4$), filtered and concentrated in vacuo. The residue was purified by SiO$_2$ chromatography eluting with a EtOAc/hexane gradient (0 to 5% EtOAc) to afford 3.34 g (98.5%) of 82.

step 2—To a solution of 82 (3.33 g, 15 mmol) and benzene (150 mL) in a dried flask was added sequentially Bu$_3$SnH (6.625 g, 22 mmol) and AIBN (0.241 g) and the resulting solution heated at reflux overnight. The reaction mixture was cooled to RT, a 10% KF solution was added and the resulting two-phase mixture stirred vigorously for 2 h. The phases were separated and the organic phase was sequentially washed with sat'd NaHCO$_3$ (50 mL) and brine. The combined organic extracts were dried (Na$_2$SO$_4$), filtered and evaporated. The crude product was purified by SiO$_2$ chromatography eluting with a DCM/hexane gradient (0 to 10% DCM) to afford 1.855 g (85%) of 84.

step 3—To a solution of iodine (2.055 g, 8 mmol) and EtOH (30 mL) was added a solution of silver sulfate (2.525 g, 8 mmol) and a solution of 84 (1.200 g, 8 mmol) in EtOH (10 mL). The brown solution was stirred for 2.5 h at RT. The resulting suspension was filtered through CELITE, the pad rinsed with EtOH and the filtrate concentrated. The crude product was purified by SiO$_2$ chromatography eluting with a DCM/hexane gradient (0 to 10% DCM) to afford 2.001 g (90.5%) of 86.

step 4—To a solution of 86 (2.00 g, 7 mmol) and HOAc (18 mL) in a dried flask was cooled to 0° C. and Br$_2$ was added dropwise over 10 min. The reaction was stirred at RT overnight. Excess bromine was quenched with 10% aq. Na$_2$S$_2$O$_3$ (20 mL) and the HOAc was evaporated. The residue was extracted with Et$_2$O and the organic extract washed with sat'd. NaHCO$_3$. The aqueous phase was back-extracted with Et$_2$O and the combined extracts washed sequentially with NaHCO$_3$ (2×20 mL), H$_2$O and brine, dried (Na$_2$SO$_4$), filtered and concentrated. The residue was purified by SiO$_2$ chromatography eluting with a DCM/hexane gradient (0 to 10% DCM) to afford 1.5960 g (71.5%) of 88.

N-{4-[(E)-2-(3,3,5-Trimethyl-2,6-dioxo-borinan-1-yl)-vinyl]-phenyl}-methanesulfonamide (89)—To a solution of Pd(OAc)$_2$ (0.076 g) and tris-(ortho-tolyl)-phosphine (0.246 g, 1 mmol) and toluene (16 mL) were added sequentially N-(4-iodo-phenyl)-methanesulfonamide (2.00 g, 7 mmol, CASRN 102294-59-7), tributyl amine (1.92 mL) and 4,4,6-trimethyl-2-vinyl-[1,3,2]dioxaborinane (1.244 g, 8 mmol) and the reaction was heated at reflux for 72 h. The reaction was cooled to RT and partitioned between Et$_2$O (100 mL) and 1M HCl (20 mL). The aqueous layer was withdrawn and re-extracted with Et$_2$O. The organic phases were washed sequentially with H$_2$O and brine. The extracts were combined, dried (Na$_2$SO$_4$), filtered and evaporated. The residue was purified by SiO$_2$ chromatography eluting with an EtOAc/hexane gradient (0 to 30% EtOAc) to afford 1.4 g (58%) of (89).

step 5—A microwave tube was charged with 88 (0.068 g), 89 (0.078 g), Na$_2$CO$_3$ (0.064 g), Pd(PPh$_3$)$_4$ (0.023 g), MeOH (1.8 mL) and DCM (0.6 mL). The tube was flushed with argon, sealed and irradiated in a microwave synthesizer at 125° C. for 40 min. The reaction mixture was cooled and concentrated in vacuo. The residue was partitioned between DCM (25 mL) and H$_2$O (5 mL). The organic layer was washed with brine (5 mL). The aqueous phase was twice extracted with DCM (25 mL). The organic layers were combined, dried (Na$_2$SO$_4$), filtered and evaporated. The crude product was purified by SiO$_2$ chromatography eluting with a EtOAc/hexane gradient (0 to 60% EtOAc) to afford 0.175 g (18%) of 90.

step 6—Introduction of the cyclopropyl group is carried out in accord with the procedure described in step 2 of example 1 to afford 92. Introduction of the pyridazinone ring (step 7) is accomplished by coupling 54 and 92 in accord with the procedure in step 3 of example 5 to afford 100.

EXAMPLE 10

HCV NS5B RNA Polymerase Activity

The enzymatic activity of HCV polymerase (NS5B570n-Con1) was measured as the incorporation of radiolabeled nucleotide monophosphates into acid insoluble RNA products. Unincorporated radiolabeled substrate was removed by filtration and scintillant was added to the washed and dried filter plate containing radiolabeled RNA product. The amount of RNA product generated by NS5B570-Con1 at the end of the reaction was directly proportional to the amount of light emitted by the scintillant.

The N-terminal 6-histidine tagged HCV polymerase, derived from HCV Con1 strain, genotype 1b (NS5B570n-Con1) contains a 21 amino acid deletion at the C-terminus relative to the full-length HCV polymerase and was purified from E. coli strain BL21(DE) pLysS. The construct, containing the coding sequence of HCV NS5B Con1 (GenBank accession number AJ242654) was inserted into the plasmid construct pET17b, downstream of a T7 promoter expression cassette and transformed into E. coli. A single colony was grown overnight as a starter culture and later used inoculate 10 L of LB media supplemented with 100 μg/mL ampicillin at 37° C. Protein expression was induced by the addition of 0.25 mM isopropyl-β-D-thiogalactopyranoside (IPTG) when optical density at 600 nM of the culture was between 0.6 and 0.8 and cells were harvested after 16 to 18 h at 30° C. NS5B570n-Con1 was purified to homogeneity using a three-step protocol including subsequent column chromatography on Ni-NTA, SP-Sepharose HP and Superdex 75 resins.

Each 50 μl enzymatic reaction contained 20 nM RNA template derived from the complementary sequence of the Internal Ribosome Entry Site (cIRES), 20 nM NS5B570n-Con1 enzyme, 0.5 μCi of tritiated UTP (Perkin Elmer catalog no. TRK-412; specific activity: 30 to 60 Ci/mmol; stock solution concentration from 7.5×10-5 M to 20.6×10-6 M), 1 μM each ATP, CTP, and GTP, 40 mM Tris-HCl pH 8.0, 40 mM NaCl, 4 mM DTT (dithiothreitol), 4 mM MgCl$_2$, and 5 µl of compound serial diluted in DMSO. Reaction mixtures were assembled in 96-well filter plates (cat #MADVN0B, Millipore Co.) and incubated for 2 h at 30° C. Reactions were stopped by addition of 10% final (v/v) trichloroacetic acid and incubated for 40 min at 4° C. Reactions were filtered, washed with 8 reaction volumes of 10% (v/v) trichloroacetic acetic acid, 4 reaction volumes of 70% (v/v) ethanol, air dried, and 25 µl of scintillant (Microscint 20, Perkin-Elmer) was added to each reaction well.

The amount of light emitted from the scintillant was converted to counts per minute (CPM) on a Topcount® plate reader (Perkin-Elmer, Energy Range: Low, Efficiency Mode Normal, Count Time: 1 min, Background Subtract: none, Cross talk reduction: Off).

Data was analyzed in Excel® (Microsoft) and ActivityBase® (Idbs®). The reaction in the absence of enzyme was used to determine the background signal, which was subtracted from the enzymatic reactions. Positive control reactions were performed in the absence of compound, from which the background corrected activity was set as 100% polymerase activity. All data was expressed as a percentage of the positive control. The compound concentration at which the enzyme-catalyzed rate of RNA synthesis was reduced by 50% (IC$_{50}$) was calculated by fitting $$Y = \% \text{ Min} + \frac{(\% \text{ Max} - \% \text{ Min})}{\left[1 + \frac{X}{(IC_{50})^S}\right]} \quad (i)$$

equation (i) to the data where "Y" corresponds to the relative enzyme activity (in %), "% Min" is the residual relative activity at saturating compound concentration, "% Max" is the relative maximum enzymatic activity, "X" corresponds to the compound concentration, and "S" is the Hill coefficient (or slope).

EXAMPLE 11

HCV Replicon Assay

This assay measures the ability of the compounds of formula I to inhibit HCV RNA replication, and therefore their potential utility for the treatment of HCV infections. The assay utilizes a reporter as a simple readout for intracellular HCV replicon RNA level. The *Renilla luciferase* gene was introduced into the first open reading frame of a genotype 1b replicon construct NK5.1 (N. Krieger et al., *J. Virol.* 2001 75(10):4614), immediately after the internal ribosome entry site (IRES) sequence, and fused with the neomycin phosphotransferase (NPTII) gene via a self-cleavage peptide 2A from foot and mouth disease virus (M. D. Ryan & J. Drew, *EMBO* 1994 13(4):928-933). After in vitro transcription the RNA was electroporated into human hepatoma Huh7 cells, and G418-resistant colonies were isolated and expanded. Stably selected cell line 2209-23 contains replicative HCV subgenomic RNA, and the activity of *Renilla luciferase* expressed by the replicon reflects its RNA level in the cells. The assay was carried out in duplicate plates, one in opaque white and one in transparent, in order to measure the anti-viral activity and cytotoxicity of a chemical compound in parallel ensuring the observed activity is not due to decreased cell proliferation or due to cell death.

HCV replicon cells (2209-23), which express *Renilla luciferase* reporter, were cultured in Dulbecco's MEM (Invitrogen cat no. 10569-010) with 5% fetal bovine serum (FBS, Invitrogen cat. no. 10082-147) and plated onto a 96-well plate at 5000 cells per well, and incubated overnight. Twenty-four hours later, different dilutions of chemical compounds in the growth medium were added to the cells, which were then further incubated at 37° C. for three days. At the end of the incubation time, the cells in white plates were harvested and luciferase activity was measured by using the *R. luciferase* Assay system (Promega cat no. E2820). All the reagents described in the following paragraph were included in the manufacturer's kit, and the manufacturer's instructions were followed for preparations of the reagents. The cells were washed once with 100 µl of phosphate buffered saline (pH 7.0) (PBS) per well and lysed with 20 µl of 1× *R. luciferase* Assay lysis buffer prior to incubation at room temperature for 20 min. The plate was then inserted into the Centro LB 960 microplate luminometer (Berthold Technologies), and 100 µl of *R. luciferase* Assay buffer was injected into each well and the signal measured using a 2-second delay, 2-second measurement program. IC$_{50}$, the concentration of the drug required for reducing replicon level by 50% in relation to the untreated cell control value, can be calculated from the plot of percentage reduction of the luciferase activity vs. drug concentration as described above.

WST-1 reagent from Roche Diagnostic (cat no. 1644807) was used for the cytotoxicity assay. Ten microliter of WST-1 reagent was added to each well of the transparent plates including wells that contain media alone as blanks. Cells were then incubated for 2 h at 37° C., and the OD value was measured using the MRX Revelation microtiter plate reader (Lab System) at 450 nm (reference filter at 650 nm). Again CC$_{50}$, the concentration of the drug required for reducing cell proliferation by 50% in relation to the untreated cell control value, can be calculated from the plot of percentage reduction of the WST-1 value vs. drug concentration as described above.

TABLE II

| Compound | Replicon IC$_{50}$ (µM) | Cytotoxicity CC$_{50}$ |
|---|---|---|
| I-2 | 0.109 | 15 |
| I-4 | 0.078 | 32.8 |

EXAMPLE 12

Pharmaceutical compositions of the subject compounds for administration via several routes were prepared as described in this Example.

| Composition for Oral Administration (A) | |
|---|---|
| Ingredient | % wt./wt. |
| Active ingredient | 20.0% |
| Lactose | 79.5% |
| Magnesium stearate | 0.5% |

The ingredients are mixed and dispensed into capsules containing about 100 mg each; one capsule would approximate a total daily dosage.

| Composition for Oral Administration (B) | |
|---|---|
| Ingredient | % wt./wt. |
| Active ingredient | 20.0% |
| Magnesium stearate | 0.5% |
| Crosscarmellose sodium | 2.0% |
| Lactose | 76.5% |
| PVP (polyvinylpyrrolidine) | 1.0% |

The ingredients are combined and granulated using a solvent such as methanol. The formulation is then dried and formed into tablets (containing about 20 mg of active compound) with an appropriate tablet machine.

| Composition for Oral Administration (C) | |
|---|---|
| Ingredient | % wt./wt. |
| Active compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water | q.s. to 100 ml |

The ingredients are mixed to form a suspension for oral administration.

| Parenteral Formulation (D) | |
|---|---|
| Ingredient | % wt./wt. |
| Active ingredient | 0.25 g |
| Sodium Chloride | qs to make isotonic |
| Water for injection to | 100 ml |

The active ingredient is dissolved in a portion of the water for injection. A sufficient quantity of sodium chloride is then added with stirring to make the solution isotonic. The solution is made up to weight with the remainder of the water for injection, filtered through a 0.2 micron membrane filter and packaged under sterile conditions.

The features disclosed in the foregoing description, or the following claims, expressed in their specific forms or in terms of a means for performing the disclosed function, or a method or process for attaining the disclosed result, as appropriate, may, separately, or in any combination of such features, be utilized for realizing the invention in diverse forms thereof.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

The patents, published applications, and scientific literature referred to herein establish the knowledge of those skilled in the art and are hereby incorporated by reference in their entirety to the same extent as if each was specifically and individually indicated to be incorporated by reference. Any conflict between any reference cited herein and the specific teachings of this specifications shall be resolved in favor of the latter. Likewise, any conflict between an art-understood definition of a word or phrase and a definition of the word or phrase as specifically taught in this specification shall be resolved in favor of the latter.

We claim:

1. A compound selected from the group consisting of:
   N-(4-{2-[3-tert-Butyl-2-methoxy-5-(2-oxo-1,2-dihydro-pyridin-3-yl)-phenyl]-cyclopropyl}-phenyl)-methanesulfonamide;
   N-(4-{2-[3-tert-Butyl-5-(2-oxo-1,2-dihydro-pyridin-3-yl)-phenyl]-cyclopropyl}-phenyl)-methanesulfonamide;
   N-(4-{2-[3-tert-Butyl-2-methoxy-5-(2-oxo-1,2-dihydro-pyridin-3-yl)-phenyl]-trans-cyclopropyl}-phenyl)-methanesulfonamide;
   N-(4-{2-[3-tert-Butyl-2-methoxy-5-(2-oxo-1,2-dihydro-pyridin-3-yl)-phenyl]-cis-cyclopropyl}-phenyl)-methanesulfonamide; and,
   N-(4-{2-[5-tert-Butyl-2-hydroxy-3-(2-oxo-1,2-dihydro-pyridin-3-yl)-phenyl]-cyclopropyl}-phenyl)-methanesulfonamide, or,
a pharmaceutically acceptable salt thereof.

* * * * *